United States Patent [19]

Wellinga et al.

[11] Patent Number: 4,927,452
[45] Date of Patent: May 22, 1990

[54] 1-CARBONYL-2-PYRAZOLINE DERIVATIVES HAVING HERBICIDAL ACTIVITY

[75] Inventors: Kobus Wellinga; Jacobus H. H. Eussen, both of Weesp, Netherlands

[73] Assignee: Duphar International Research B.V., Weesp, Netherlands

[21] Appl. No.: 277,529

[22] Filed: Nov. 28, 1988

Related U.S. Application Data

[63] Continuation of Ser. No. 113,659, Oct. 28, 1987, abandoned.

[30] Foreign Application Priority Data

Oct. 31, 1986 [NL] Netherlands ............... 8602746

[51] Int. Cl.$^5$ ............... A01N 43/56; C07D 231/06; C07D 231/08
[52] U.S. Cl. ............... 71/92; 71/90; 548/374; 548/369; 548/379
[58] Field of Search ............... 71/92, 90; 548/374, 548/379, 369

[56] References Cited

U.S. PATENT DOCUMENTS 3,780,058 12/1973 Brzozowski et al. ............... 548/379

Primary Examiner—John M. Ford
Attorney, Agent, or Firm—Stevens, Davis, Miller & Mosher

[57] ABSTRACT

The invention relates to a herbicidally active compound of the general

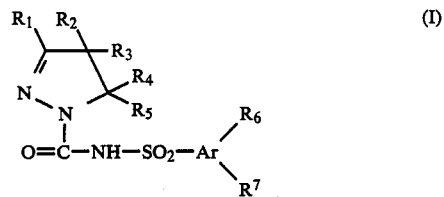

wherein
$R_1$, $R_2$, $R_3$ and $R_4$ are equal or different and represent hydrogen atoms, alkyl groups having 1–6 carbon atoms, cycloalkyl groups having 3–6 carbon atoms or alkoxycarbonyl groups having 2–5 carbon atoms;
$R_5$ is a hydrogen atom, an alkyl group or haloalkyl group having 1–8 carbon atoms, a substituted or non-substituted phenyl group, a substituted or non-substituted heterocyclic group, or an alkenyl, alkynyl or alkoxycarbonyl group having 2–5 carbon atoms;
and wherein two of the groups $R_1$, $R_2$, $R_3$, $R_4$ and $R_5$ together may form a straight or branched alkylene group having 3–5 carbon atoms;
Ar is a phenyl group, a phenyl ($C_1$-$C_4$)alkyl group or a heteroaryl group;
$R_6$ is a hydrogen atom or substituent to Ar, which substituent, in case Ar is a phenyl or phenylalkyl group, is attached to the phenyl group in the ortho position with respect to the sulphonyl or sulphonylalkyl group, and which substituent is selected from the following atoms and groups: a halogen atom; a nitro group; an alkoxycarbonyl group that has 2–8 carbon atoms and is unsubstituted or substituted with one or more hydroxy or $C_1$-$C_4$ alkoxy groups; and an alkyl, hydroxyalkyl, haloalkyl, alkoxy, haloalkoxy, alkylthio, haloalkylthio, alkylsulphonyl and haloalkylsulphonyl group having 1–6 carbon atoms; and
$R_7$ represent a hydrogen atom or one or two halogen atoms or $C_1$-$C_4$ alkyl groups.

10 Claims, No Drawings

1-CARBONYL-2-PYRAZOLINE DERIVATIVES HAVING HERBICIDAL ACTIVITY

This application is a continuation of application Ser. No. 113,659, filed Oct. 28, 1987, now abandoned.

The invention relates to new 1-carbamoyl-2-pyrazoline derivatives and to a method of preparing the new compounds. The invention also relates to compositions based on the new compounds and having herbicidal and/or plant growth regulating activity and to the use of said compositions to prevent and/or control undesired plant growth.

Plants which in a given situation are considered to be undesired may be termed weeds. In general, weed control may be carried out after or prior to emergence of the weeds; agents whose object is to control the weeds after their emergence are termed post-emergence herbicides, the other ones are termed pre-emergence herbicides. So, for controlling or preventing weeds, the weed plants themselves or the plots in which they occur may be treated. In agriculture, horticulture and forestry both types of herbicides are used, if so necessary, for the uninhibited growth of the crop during the whole growth period. However, it is to be preferred to use one single application which, when a pre-emergence herbicide is used, is usually carried out prior to, simultaneously with or immediately after sowing or planting the crop, and, when a post-emergence herbicide is used, before the emerged weeds start hindering the growth of the crop. Pre-emergence herbicides are usually applied before the crop is standing, so that damage to the crop is avoided when the herbicide is used. Moreover, sowing of the crop and providing the herbicide in the soil destined for the crop can be carried out in one operation. On the other hand, post-emergence herbicides can often be used more efficiently.

It stands to reason that in addition to the activity also the selectivity of the herbicide used is of great importance. In fact, the undesired plants must be controlled or the growth of the undesired plants must be suppressed, but the growth of the crop may not be detrimentally influenced by the herbicide used. An ideal herbicide must control the weeds in the crop during the whole growth season of the crop after a single application in a low dosage. The herbicide must be capable of not only controlling all types of weeds, but also of killing both the seedlings and the growing plants of these weeds, as well as preventing the germination of the weed seeds. However, the herbicide may not exert any detrimental influence on the crops on which it has been provided.

It will be obvious that none of the herbicides presently in use can satisfy these conditions simultaneously and hence is ideal. Effective weed control is usually associated with noticeable damage to the crop, while a herbicide which in a given dosage does not have any detrimental influence on the crop usually does not effectively control all the weeds in the same dosage. It will be clear from the above that small differences in herbicidal activity and in influence on the crop may already be of great importance in the evaluation of herbicides for their practical applicability.

In agriculture and horticulture it is often desired to control the growth of trees, shrubs or non-woody plants, or parts thereof. It may be necessary, for example, to inhibit the growth of plants, such as fruit trees, hedge shrubs or lawn grass. It may also be advantageous to influence the growth of parts of plants, for example, by inhibiting the growth of the terminal buds of sugar cane so that the stems can develop better and the yield of sugar is increased. It may also be of importance to inhibit or suppress the development of suckers, in particular in those plants in which the formation of suckers frequently occurs, for example, in various ornamental plants, in tomato plants and in tobacco plants. Said suckers consume much nutrient which consequently does not favour the development of other parts of the plants, for example, the leaves, flowers and fruits. In the case of tobacco plants it is frequently necessary to inhibit suckers to a considerable extent because the size and quality of the tobacco plant or plants is very adversely influenced by the development of suckers, and in practice for large plots containing many tobacco plants the manual removal of the suckers is both time-consuming and expensive.

1-Carbamoyl-2-pyrazoline derivatives having insecticidal activity are known from literature, e.g. 1-(4-chlorophenylcarbamoyl)-3-(4-chlorophenyl)-2-pyrazoline and 1-(2-chlorophenylcarbamoyl)-3,5-bis(4-chlorophenyl)-2-pyrazoline are known from U.S. patent specification No. 4,095,026, e.g. 1-(3-trifluoromethylphenylcarbamoyl)-3-(4-chlorophenyl)-4-phenyl-2-pyrazoline from U.S. patent specification No. 4,070,365, and e.g. 1-(4-methoxycarbonylphenylcarbamoyl)-3-(4-chlorophenyl)-4-(4-cyanobutyl)-2-pyrazoline from European patent specification No. 65334. None of these compounds, nor other compounds known from these or related patent specifications, however, show any herbicidal activity in a dosage conventionally used for herbicidal application.

It has now been found that an 1-carbamoyl-2-pyrazoline derivative of the general formula

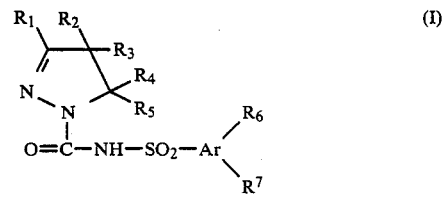

wherein
$R_1$, $R_2$, $R_3$ and $R_4$ are equal or different and represent hydrogen atoms, alkyl groups having 1-6 carbon atoms, cycloalkyl groups having 3-6 carbon atoms or alkoxycarbonyl groups having 2-5 carbon atoms;
$R_5$ is a hydrogen atom, an alkyl group or haloalkyl group having 1-8 carbon atoms, a substituted or non-substituted phenyl group, a substituted or non-substituted heterocyclic group, or an alkenyl, alkynyl or alkoxycarbonyl group having 2-5 carbon atoms;
and wherein two of the groups $R_1$, $R_2$, $R_3$, $R_4$ and $R_5$ together may form a straight or branched alkylene group having 3-5 carbon atoms;
Ar is a phenyl group, a phenyl($C_1$–$C_4$)alkyl group or a heteroaryl group;
$R_6$ is a hydrogen atom or substituent on Ar, which substituent, in case Ar is a phenyl or phenylalkyl group, is attached to the phenyl group in the ortho position with respect to the sulphonyl or sulphonylalkyl group, and which substituent is selected from the following atoms and groups: a halogen atoms; a nitro group; an alkoxycarbonyl group that has 2-8 carbon atoms and is unsubstituted or substituted with one or more hydroxy or $C_1$–$C_4$ alkoxy groups; and an alkyl, hydroxyalkyl, haloalkyl, alkoxy, haloalkoxy, alkylthio, haloalkylthio, alkylsulphonyl and haloalkylsulphonyl group having 1-6 carbon atoms; and R$_7$ represents a hydrogen atom or one or two halogen atoms or C$_1$-C$_4$ alkyl groups;

or a salt of this compound with an inorganic or organic base; shows an interesting herbicidal activity. The term "herbicidal" should be interpreted broadly and also includes plant growth regulating. If in the above formula I R$_5$ is a heterocyclic group, this group may be selected from various heterocyclic groups, for example *furyl, thienyl*, etc. If Ar is a heteroaryl group, this group may be chosen from various heteroaromatic groups, for example, thienyl, pyrazolyl, etc. If R$_5$ represents a substituted phenyl or heterocyclic group, the substituents may be chosen from various atoms and groups, for example, halogen, nitro, C$_1$-C$_4$ haloalkyl, C$_1$-C$_4$ alkoxy, C$_1$-C$_4$ haloalkoxy, etc.

1-Carbamoyl-2-pyrazoline derivatives having hypoglycemic activity are known from Netherlands patent application 7112819, U.S. Pat. No. 3,887,709 and Chemical Abstracts Vol. 82, 1975, no. 11, 72861 and 72862. Therefore the present invention does not include compounds of the above general formula I, wherein, if Ar is a phenyl group and R$_6$ is a hydrogen atom, R$_7$ is a hydrogen atom or a halogen atom in the para position with regard to the sulphonyl group.

If both activity and selectivity are to be taken into account, a compound of the general formula

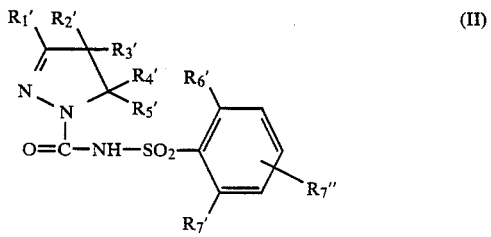

wherein

R$_1'$, R$_2'$, R$_3'$ are equal or different and represent hydrogen atoms or alkyl groups having 1-4 carbon atoms, or wherein R$_1'$ together with R$_2'$, or R$_3'$ together with R$_4'$ form a tetramethylene group, R$_5'$ is a hydrogen atom, a halogenated or non-halogenated alkyl group having 1-8 carbon atoms, a phenyl group, or a phenyl group substituted with halogen, nitro, C$_1$-C$_4$ alkyl or C$_1$-C$_4$ alkoxy, R$_6'$ is a halogen atom, a nitro group, an alkoxycarbonyl group having 2-5 carbon atoms or haloalkyl, alkoxy, haloalkoxy, alkylthio, haloalkylthio or alkylsulphonyl group having 1-4 carbon atoms, and R$_7'$ and R$_7''$ are equal or different and represent hydrogen atoms or halogen atoms, or a salt of this compound with an inorganic or organic base, can be considered to be particularly suitable.

From the last-mentioned compounds is to be preferred a compound of the general formula

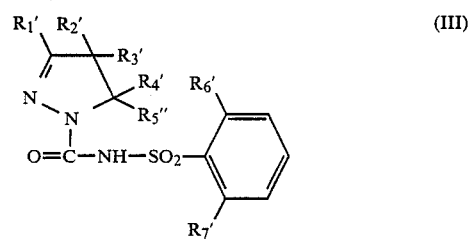

wherein

R$_1'$, R$_2'$, R$_3'$, R$_4'$, R$_6'$ and R$_7'$ have the above meanings, and

R$_5''$ is a phenyl group or a phenyl group substituted with halogen or nitro.

In addition to the 5-phenyl substituted 2-pyrazoline compounds mentioned hereinafter under nos. (47), (48) and (62), the 2-pyrazoline compounds mentioned hereinafter under nos. (8), (23), (27), (31), (85) and (86) have proved to be pre-eminently suitable as herbicides.

Examples of 1-carbamoyl-2-pyrazoline derivatives which may be used in herbicidal compositions according to the invention are:

(1) 1-(2-trifluoromethylphenylsulphonycarbamoyl)-2-pyrazoline, (2) 1-(2-methoxycarbonylphenylsulphonylcarbamoyl)-2-pyrazoline, (3) 1-(2-chlorophenylsulphonylcarbamoyl)-2-pyrazoline, (4) 1-(2,6-dichlorophenylsulphonylcarbamoyl)-2-pyrazoline, (5) 1-(2,4,6-trichlorophenylsulphonylcarbamoyl)-2-pyrazoline, (6) 1-(2-chlorophenylsulphonylcarbamoyl)-5-n-propyl-2-pyrazoline (7) 1-(2-trifluoromethylphenylsulphonylcarbamoyl)-3-methyl-2-pyrazoline, (8) 1-(2-methoxycarbonylphenylsulphonylcarbamoyl)-3-methyl-2-pyrazoline, (9) 1-(2-chlorophenylsulphonylcarbamoyl)-3-methyl-2-pyrazoline,

(10) 1-(2,6-dichlorophenylsulphonylcarbamoyl)-3-methyl-2-pyrazoline,

(11) 1-phenylsulphonylcarbamoyl-5-n-propyl-2-pyrazoline,

(12) 1-(2-trifluoromethylphenylsulphonylcarbamoyl)-3-ethyl-2-pyrazoline,

(13) 1-(2-methoxycarbonylphenylsulphonylcarbamoyl)-3-ethyl-2-pyrazoline,

(14) 1-(2-chlorophenylsulphonylcarbamoyl)-3-ethyl-2-pyrazoline,

(15) 1-(2,6-dichlorophenylsulphonylcarbamoyl)-3-ethyl-2-pyrazoline,

(16) 1-(2-trifluoromethylphenylsulphonylcarbamoyl)-5-methyl-2-pyrazoline,

(17) 1-(2-methoxycarbonylphenylsulphonylcarbamoyl)-5-methyl-2-pyrazoline,

(18) 1-(2-chlorophenylsulphonylcarbamoyl)-5-methyl-2-pyrazoline,

(19) 1-(2,6-dichlorophenylsulphonylcarbamoyl)-5-methyl-2-pyrazoline,

(20) 1-(2,4,6-trichlorophenylsulphonylcarbamoyl)-5-methyl-2-pyrazoline,

(21) 1-(2,6-difluorophenylsulphonylcarbamoyl)-5-methyl-2-pyrazoline,

(22) 1-(2-trifluoromethylphenylsulphonylcarbamoyl)-5-ethyl-2-pyrazoline,
(23) 1-(2-methoxycarbonylphenylsulphonylcarbamoyl)-5-ethyl-2-pyrazoline,
(24) 1-(2-chlorophenylsulphonylcarbamoyl)-5-ethyl-2-pyrazoline,
(25) 1-(2,6-dichlorophenylsulphonylcarbamoyl)-5-ethyl-2-pyrazoline,
(26) 1-(2-trifluoromethylphenylsulphonylcarbamoyl)-5-n-propyl-2-pyrazoline,
(27) 1-(2-methoxycarbonylphenylsulphonylcarbamoyl)-5-n-propyl-2-pyrazoline,
(28) 1-(2-fluorophenylsulphonylcarbamoyl)-5-n-propyl-2-pyrazoline,
(29) 1-(2,6-dichlorophenylsulphonylcarbamoyl)-5-n-propyl-2-pyrazoline,
(30) 1-(2,6-difluorophenylsulphonylcarbamoyl)-2-pyrazoline,
(31) 1-(2-methoxycarbonylphenylsulphonylcarbamoyl)-4,5-dimethyl-2-pyrazoline,
(32) 1-(2-chlorophenylsulphonylcarbamoyl)-4,5-dimethyl-2-pyrazoline,
(33) 1-(2-methoxycarbonylphenylsulphonylcarbamoyl)-4-methyl-5-ethyl-2-pyrazoline,
(34) 1-(2-trifluoromethylphenylsulphonylcarbamoyl)-4-ethyl-5-methyl-2-pyrazoline,
(35) 1-(2-methoxycarbonylphenylsulphonylcarbamoyl)-4-ethyl-5-methyl-2-pyrazoline,
(36) 1-(2-chlorophenylsulphonylcarbamoyl)-4-ethyl-5-methyl-2-pyrazoline,
(37) 1-(2,6-dichlorophenylsulphonylcarbamoyl)-4-ethyl-5-methyl-2-pyrazoline,
(38) 1-(3-chlorophenylsulphonylcarbamoyl)-4-ethyl-5-methyl-2-pyrazoline,
(39) 1-(2-methylphenylsulphonylcarbamoyl)-5,5-dimethyl-2-pyrazoline,
(40) 1-(2-methoxycarbonylphenylsulphonylcarbamoyl)-3,5,5-trimethyl-2-pyrazoline,
(41) 1-(2-chlorophenylsulphonylcarbamoyl)-3,5,5-trimethyl-2-pyrazoline,
(42) 1-(2-fluorophenylsulphonylcarbamoyl)-3,5,5-trimethyl-2-pyrazoline,
(43) 1-(2,6-dichlorophenylsulphonylcarbamoyl)-3,5,5-trimethyl-2-pyrazoline,
(44) 1-(2,6-difluorophenylsulphonylcarbamoyl)-3,5,5-trimethyl-2-pyrazoline,
(45) 2-(2,4,5-trichlorophenylsulphonylcarbamoyl)-3,5,5-trimethyl-2-pyrazoline,
(46) 1-(2,4,6-trichlorophenylsulphonylcarbamoyl)-3,5,5-trimethyl-2-pyrazoline,
(47) 1-(2-chlorophenylsulphonylcarbamoyl)-5-phenyl-2-pyrazoline,
(48) 1-(2-trifluoromethylphenylsulphonylcarbamoyl)-5-phenyl-2-pyrazoline,
(49) 1-(2-methoxycarbonylphenylsulphonylcarbamoyl)-5-phenyl-2-pyrazoline,
(50) 1-(2-trifluoromethylphenylsulphonylcarbamoyl)-5,5-dimethyl-2-pyrazoline,
(51) 1-phenylsulphonylcarbamoyl-3-methyl-2-pyrazoline,
(52) 1-phenylsulphonylcarbamoyl-3-ethoxycarbonyl-5-methoxycarbonyl-5-methyl-2-pyrazoline,
(53) 1-(2-chlorophenylsulphonylcarbamoyl)-3-ethoxycarbonyl-5-methoxycarbonyl-5-methyl-2-pyrazoline,
(54) 1-(2-methylphenylsulphonylcarbamoyl)-3-methyl-2-pyrazoline,
(55) 1-(2-methylphenylsulphonylcarbamoyl)-4-ethyl-5-methyl-2-pyrazoline,
(56) 1-(2,6-dichlorophenylsulphonylcarbamoyl)-5,5-dimethyl-2-pyrazoline,
(57) 1-(3-chlorophenylsulphonylcarbamoyl)-5,5-dimethyl-2-pyrazoline,
(58) 1-(2-methoxycarbonylphenylsulphonylcarbamoyl)-4-methyl-2-pyrazoline,
(59) 1-(2-trifluoromethylphenylsulphonylcarbamoyl)-4-methyl-2-pyrazoline,
(60) 1-(2-bromophenylsulphonylcarbamoyl)-5-phenyl-2-pyrazoline,
(61) 1-(2,6-dichlorophenylsulphonylcarbamoyl)-5-phenyl-2-pyrazoline,
(62) 1-(2,6-difluorophenylsulphonylcarbamoyl)-5-phenyl-2-pyrazoline,
(63) 1-(2,6-difluorophenylsulphonylcarbamoyl)-5,5-dimethyl-2-pyrazoline,
(64) 1-(2,5-dimethylphenylsulphonylcarbamoyl)-5,5-dimethyl-2-pyrazoline,
(65) 1-phenylsulphonylcarbamoyl-3-methyl-5-n-butyl-2-pyrazoline,
(66) 1-(2-chlorophenylsulphonylcarbamoyl)-4-methyl-2-pyrazoline,
(67) 1-(2-methylphenylsulphonylcarbamoyl)-4-methyl-2-pyrazoline,
(68) 1-(2,5-dimethylphenylsulphonylcarbamoyl)-4-methyl-2-pyrazoline,
(69) 1-(2-chlorobenzylsulphonylcarbamoyl)-3-methyl-2-pyrazoline,
(70) 1-(2-bromophenylsulphonylcarbamoyl)-2-pyrazoline,
(71) 1-(5-chlorothienyl-2-sulphonylcarbamoyl)-2-pyrazoline,
(72) 1-(2,6-difluorophenylsulphonylcarbamoyl)-4-methyl-2-pyrazoline,
(73) 1-phenylsulphonylcarbamoyl-5,5-dimethyl-2-pyrazoline,
(74) 1-(2-methoxycarbonylphenylsulphonylcarbamoyl)-5,5-dimethyl-2-pyrazoline,
(75) 1-phenylsulphonylcarbamoyl-5-phenyl-2-pyrazoline,
(76) 1-(2-methylphenylsulphonylcarbamoyl)-5-phenyl-2-pyrazoline,
(77) 1-(2-bromophenylsulphonylcarbamoyl)-5,5-dimethyl-2-pyrazoline,
(78) 1-(2-bromophenylsulphonylcarbamoyl)-3-methyl-2-pyrazoline,
(79) 1-(5-chlorothienyl-2-sulphonylcarbamoyl)-3-methyl-2-pyrazoline,
(80) 1-(5-chlorothienyl-2-sulphonylcarbamoyl)-5-methyl-2-pyrazoline,
(81) 1-(2-chlorophenylsulphonylcarbamoyl)-5,5-dimethyl-2-pyrazoline,
(82) 1-(2,4,6-trichlorophenylsulphonylcarbamoyl)-5,5-dimethyl-2-pyrazoline,
(83) 1-phenylsulphonylcarbamoyl-4-ethyl-2-pyrazoline,
(84) 1-(2-chlorophenylsulphonylcarbamoyl)-4-ethyl-2-pyrazoline,
(85) 1-(2-methoxycarbonylphenylsulphonylcarbamoyl)-4-ethyl-2-pyrazoline,
(86) 1-(2-trifluoromethylphenylsulphonylcarbamoyl)-4-ethyl-2-pyrazoline,
(87) 1-(2,6-difluorphenylsulphonylcarbamoyl)-4-ethyl-2-pyrazoline,
(88) 1-(2-bromophenylsulphonylcarbamoyl)-5-methyl-2-pyrazoline,

(89) 1-(2-bromophenylsulphonylcarbamoyl)-5-ethyl-2-pyrazoline,
(90) 1-(2-bromophenylsulphonylcarbamoyl)-5-n-propyl-2-pyrazoline,
(91) 1-(2-bromophenylsulphonylcarbamoyl)-3-methyl-5-n-butyl-2-pyrazoline,
(92) 1-(2-methylphenylsulphonylcarbamoyl)-4-ethyl-2-pyrazoline,
(93) 1-(3-chlorophenylsulphonylcarbamoyl)-5-phenyl-2-pyrazoline,
(94) 1-(4-clorophenylsulphonylcarbamoyl)-5-phenyl-2-pyrazoline,
(95) 1-(2-methoxycarbonylphenylsulphonylcarbamoyl)-4-n-butyl-2-pyrazoline,
(96) 1-(2-methoxycarbonylphenylsulphonylcarbamoyl)-5-n-hexyl-2-pyrazoline,
(97) 1-(2-chlorophenylsulphonylcarbamoyl)-3,4-tetramethylene-2-pyrazoline,
(98) 1-(2-methoxycarbonylphenylsulphoncarbamoyl)-3,4-tetramethylene-2-pyrazoline,
(99) 1-phenylsulphonylcarbamoyl-5-(4-chlorophenyl)-2-pyrazoline,
(100) 1-(2-chlorophenylsulphonylcarbamoyl)-5-(4-chlorophenyl)-2-pyrazoline,
(101) 1-(2-trifluoromethylphenylsulphonylcarbamoyl)-3,4-tetramethylene-2-pyrazoline,
(102) 1-(2-bromophenylsulphonylcarbamoyl)-3,4-tetramethylene-2-pyrazoline,
(103) 1-(2,6-dichlorophenylsulphonylcarbamoyl)-3,4-tetramethylene-2-pyrazoline,
(104) 1-(2-chloro-4-fluorophenylsulphonylcarbamoyl)-3-methyl-2-pyrazoline,
(105) 1-(2,6-dichlorophenylsulphonylcarbamoyl)-3-methyl-5-isopropyl-2-pyrazoline,
(106) 1-(thienyl-2-sulphonylcarbamoyl)-3-methyl-2-pyrazoline,
(107) 1-(thienyl-2-sulphonylcarbamoyl)-4-n-butyl-2-pyrazoline,
(108) 1-(thienyl-2-sulphonylcarbamoyl)-5-phenyl-2-pyrazoline,
(109) 1-(thienyl-2-sulphonylcarbamoyl)-5-(4-chlorophenyl)-2-pyrazoline,
(110) 1-(thienyl-2-sulphonylcarbamoyl)-4-ethyl-2-pyrazoline,
(111) 1-(2,3-dichlorophenylsulphonylcarbamoyl)-5-n-propyl-2-pyrazoline,
(112) 1-(2,3-dichlorophenylsulphonylcarbamoyl)-3,5,5-trimethyl-2-pyrazoline,
(113) 1-(2,3-dichlorophenylsulphonylcarbamoyl)-5-phenyl-2-pyrazoline,
(114) 1-(2,3-dichlorophenylsulphonylcarbamoyl)-4-ethyl-2-pyrazoline,
(115) 1-(2,3-dichlorophenylsulphonylcarbamoyl)-5,5-dimethyl-2-pyrazoline,
(116) 1-(2-chlorophenylsulphonylcarbamoyl)-3,5-dimethyl-2-pyrazoline,
(117) 1-(2,6-dichlorophenylsulphonylcarbamoyl)-3,5-dimethyl-2-pyrazoline,
(118) 1-(2,6-difluorophenylsulphonylcarbamoyl)-3,5-dimethyl-2-pyrazoline,
(119) 1-(2-methoxycarbonylphenylsulphonylcarbamoyl)-5-(furyl-2-)-2-pyrazoline,
(120) 1-(2-nitrophenylsulphonylcarbamoyl)-2-pyrazoline,
(121) 1-(2-nitrophenylsulphonylcarbamoyl)-3-methyl-2-pyrazoline,
(122) 1-(2-nitrophenylsulphonylcarbamoyl)-4-methyl-2-pyrazoline,
(123) 1-(2-nitrophenylsulphonylcarbamoyl)-5-methyl-2-pyrazoline,
(124) 1-(2-nitrophenylsulphonylcarbamoyl)-5-n-propyl-2-pyrazoline,
(125) 1-(2-nitrophenylsulphonylcarbamoyl)-5-phenyl-2-pyrazoline,
(126) 1-phenylsulphonylcarbamoyl-3-methyl-5-phenyl-2-pyrazoline,
(127) 1-(2-methoxycarbonylphenylsulphonylcarbamoyl)-3-methyl-5-phenyl-2-pyrazoline,
(128) 1-(2-chlorophenylsulphonylcarbamoyl)-3-methyl-5-phenyl-2-pyrazoline,
(129) 1-(2-bromophenylsulphonylcarbamoyl)-3-methyl-5-phenyl-2-pyrazoline,
(130) 1-(2,6-dichlorophenylsulphonylcarbamoyl)-3-methyl-5-phenyl-2-pyrazoline,
(131) 1-(2,6-difluorophenylsulphonylcarbamoyl)-3-methyl-5-phenyl-2-pyrazoline,
(132) 1-(2-trifluoromethylphenylsulphonylcarbamoyl)-3-methyl-5-phenyl-2-pyrazoline,
(133) 1-(thienyl-2-sulphonylcarbamoyl)-3-methyl-5-phenyl-2-pyrazoline,
(134) 1-(2-methoxycarbonylthienyl-3-sulphonylcarbamoyl)-3,5,5-trimethyl-2-pyrazoline,
(135) 1-(2-methoxycarbonylthienyl-3-sulphonylcarbamoyl)-2-pyrazoline,
(136) 1-(2-methoxycarbonylthienyl-3-sulphonylcarbamoyl)-3-methyl-2-pyrazoline,
(137) 1-(2-methoxycarbonylthienyl-3-sulphonylcarbamoyl)-5-methyl-2-pyrazoline,
(138) 1-(2-methoxycarbonylthienyl-3-sulphonylcarbamoyl)-5-phenyl-2-pyrazoline,
(139) 1-(2-methoxyphenylsulphonylcarbamoyl)-5-phenyl-2-pyrazoline,
(140) 1-(2-methoxyphenylsulphonylcarbamoyl)-2-pyrazoline
(141) 1-(2-methoxyphenylsulphonylcarbamoyl)-5,5-dimethyl-2-pyrazoline,
(142) 1-(2-methoxyphenylsulphonylcarbamoyl)-3,5,5-trimethyl-2-pyrazoline,
(143) 1-(2-methylsulphonylphenylsulphonylcarbamoyl)-3-methyl-5-phenyl-2-pyrazoline,
(144) 1-(2-methylsulphonylphenylsulphonylcarbamoyl)-3-methyl-2-pyrazoline,
(145) 1-(2-methylsulphonylphenylsulphonylcarbamoyl)-5-phenyl-2-pyrazoline,
(146) 1-(2-ethylthiophenylsulphonylcarbamoyl)-2-pyrazoline,
(147) 1-(2-fluorophenylsulphonylcarbamoyl)-3-methyl-2-pyrazoline,
(148) 1-(2-fluorophenylsulphonylcarbamoyl)-5-phenyl-2-pyrazoline,
(149) 1-(2-ethylthiophenylsulphonylcarbamoyl)-5-phenyl-2-pyrazoline,
(150) 1-(2-fluorophenylsulphonylcarbamoyl)-3-methyl-5-phenyl-2-pyrazoline,
(151) 1-(2-ethylthiophenylsulphonylcarbamoyl)-3-methyl-5-phenyl-2-pyrazoline,
(152) 1-(2-methylsulphonylphenylsulphonylcarbamoyl)-4-ethyl-2-pyrazoline,
(153) 1-(2-methylsulphonylphenylsulphonylcarbamoyl)-5-methyl-2-pyrazoline,
(154) 1-(2-fluorophenylsulphonylcarbamoyl)-4-ethyl-2-pyrazoline,
(155) 1-(2-fluorophenylsulphonylcarbamoyl)-5,5-dimethyl-2-pyrazoline,
(156) 1-(2-chlorophenylsulphonylcarbamoyl)-3,4-tetramethylene-5-phenyl-2-pyrazoline, (157) 1-(2-fluorophenylsulphonylcarbamoyl)-3,4-tetramethylene-5-phenyl-2-pyrazoline,
(158) 1-(2-ethoxycarbonylphenylsulphonylcarbamoyl)-3,4-tetramethylene-5-phenyl-2-pyrazoline,
(159) 1-(2,6-dichlorophenylsulphonylcarbamoyl)-3,4-tetramethylene-5-phenyl-2-pyrazoline,
(160) 1-(2-trifluoromethylphenylsulphonylcarbamoyl)-3,4-tetramethylene-5-phenyl-2-pyrazoline,
(161) 1-(2,6-difluorophenylsulphonycarbamoyl)-3-methyl-2-pyrazoline,
(162) 1-(1-methyl-4-ethoxycarbonylpyrazolyl-5-sulphonylcarbamoyl)-2-pyrazoline,
(163) 1-(2-trifluoromethoxyphenylsulphonylcarbamoyl)-2-pyrazoline,
(164) 1-(2-difluoromethoxyphenylsulphonylcarbamoyl)-2-pyrazoline,
(165) 1-(1-methyl-4-ethoxycarbonylpyrazolyl-5-sulphonylcarbamoyl)-3,5,5-trimethyl-2-pyrazoline,
(166) 1-(2-trifluoromethoxyphenylsulphonylcarbamoyl)-3,5,5-trimethyl-2-pyrazoline,
(167) 1-(1-methyl-4-ethoxycarbonylpyrazolyl-5-sulphonylcarbamoyl)-5-phenyl-2-pyrazoline,
(168) 1-(2-trifluoromethoxyphenylsulphonylcarbamoyl)-5-phenyl-2-pyrazoline,
(169) 1-(2-trifluoromethoxyphenylsulphonylcarbamoyl)-3-methyl-5-phenyl-2-pyrazoline,
(170) 1-phenylsulphonylcarbamoyl-3-cyclopropyl-5-phenyl-2-pyrazoline,
(171) 1-(2-methoxycarbonylphenylsulphonylcarbamoyl)-3-cyclopropyl-5-phenyl-2-pyrazoline,
(172) 1-(2-chlorophenylsulphonylcarbamoyl)-3-cyclopropyl-5-phenyl-2-pyrazoline,
(173) 1-(2-fluorophenylsulphonylcarbamoyl)-3-cyclopropyl-5-phenyl-2-pyrazoline,
(174) 1-(2,6-dichlorophenylsulphonylcarbamoyl)-3-cyclopropyl-5-phenyl-2-pyrazoline,
(175) 1-(2,6-difluorophenylsulphonylcarbamoyl)-3-cyclopropyl-5-phenyl-2-pyrazoline,
(176) 1-(2-trifluoromethoxyphenylsulphonylcarbamoyl)-3-cyclopropyl-5-phenyl-2-pyrazoline,
(177) 1-(2-difluoromethoxyphenylsulphonylcarbamoyl)-3-cyclopropyl-5-phenyl-2-pyrazoline,
(178) 1-(2-trifluoromethylphenylsulphonylcarbamoyl)-3-cyclopropyl-5-phenyl-2-pyrazoline,
(179) 1-[2-(1,1,2,3,3,3-hexafluoropropylthio)phenylsulphonylcarbamoyl]-2-pyrazoline,
(180) 1-(2-difluoromethoxyphenylsulphonylcarbamoyl)-4-ethyl-2-pyrazoline,
(181) 1-(2-difluoromethoxyphenylsulphonylcarbamoyl)-3,5,5-trimethyl-2-pyrazoline,
(182) 1-(2-difluoromethoxyphenylsulphonylcarbamoyl)-5,5-dimethyl-2-pyrazoline,
(183) 1-[2-(1,1,2,3,3,3-hexafluoropropylthio)phenylsulphonylcarbamoyl]-3,5,5-trimethyl-2-pyrazoline,
(184) 1-(2-difluoromethoxyphenylsulphonylcarbamoyl)-5-ethyl-2-pyrazoline,
(185) 1-(2-difluoromethoxyphenylsulphonylcarbamoyl)-3-methyl-5-phenyl-2-pyrazoline,
(186) 1-(2-difluoromethoxyphenylsulphonylcarbamoyl)-3-methyl-5-n-butyl-2-pyrazoline,
(187) 1-(2-difluoromethoxyphenylsulphonylcarbamoyl)-5-phenyl-2-pyrazoline,
(188) 1-(2-bromophenylsulphonylcarbamoyl)-3-cyclopropyl-5-phenyl-2-pyrazoline,
(189) 1-(thienyl-2-sulphonylcarbamoyl)-3-cyclopropyl-5-phenyl-2-pyrazoline,
(190) 1-(2-trifluoromethylphenylsulphonylcarbamoyl)-5-(4-nitrophenyl)-2-pyrazoline,
(191) 1-(2-chlorophenylsulphonylcarbamoyl)-5-(4-nitrophenyl)-2-pyrazoline,
(192) 1-(2,6-dichlorophenylsulphonylcarbamoyl)-5-(4-nitrophenyl)-2-pyrazoline,
(193) 1-(2-methoxycarbonylphenylsulphonylcarbamoyl)-5-(4-nitrophenyl)-2-pyrazoline, and
(194) 1-(2,6-difluorophenylsulphonylcarbamoyl)-5-(4-nitrophenyl)-2-pyrazoline.

The substances according to the invention may be used for the control of undesired plant growth. Although the new compounds have an interesting pre-emergence herbicidal activity, their activity as post-emergence herbicides still is most striking. Therefore the compounds according to the invention are preferably used as post-emergence herbicides for the control of monocot weeds, for example, *Poa annua* (annual bluegrass), *Avena fatua* (wild oats), *Alopecurus myosuroides* (blackgrass), *Panicum miliaceum* (millet) and *Echinochloa crusgalli* (barnyard grass), and of dicot weeds, for example, *Galinsoga parviflora* (small-flowered g.), *Galium aparine* (cleavers), *Chenopodium album* (common lambsquarters), *Datura stramonium* (jimsonweed), *Polygonum convolvulus* (wild buckwheat), *Capsella bursa-pastoris* (shepherd's purse), *Stellaria media* (chickweed), *Senecio vulgaris* (common groundsel), *Veronica arvensis* (common speedwell), *Ipomoea purpurea* (common morning glory's), *Matricaria spp.* (mayweeds), *Amaranthus spp.* (pigweeds), *Solanum nigrum* (black nightshade), *Spergula spp.* (spurrey), *Urtica dioca* (stinging nettle), *Polygonum aviculare* (knotgrass), *Sonchus arvensis* (field sow thistle), *Silybum marianum,* (milk thistle), *Xanthium pensylvanicum, Ipomoea muricata, Ipomoea hederacea, Ipomoea lucunosa, Cassia obtusifolia, Sida spinosa, Anoda cristate, Abutilon theophrasti, Portulaca oleracea,* etc. in various crops, for example, in cereals e.g. wheat, rice, oats and barley, in maize, and in cotton.

For practical application, the substances in accordance with the invention are processed to compositions. In such compositions the active substance is mixed with solid carrier material or dissolved or dispersed in liquid carrier material, if desired in combination with auxiliary substances, for example, emulsifiers, wetting agents, dispersing agents and stabilizers.

Examples of compositions according to the invention are aqueous solutions and dispersions, oily solutions and oily dispersions, solutions in organic solvents, pastes, dusting powders, dispersing powders, miscible oils, granules and pellets.

Dispersible powders, pastes and miscible oils are compositions in concentrate form which are diluted prior to or during use.

The solutions in organic solvents are mainly used in air application, namely when large areas are treated with a comparatively small quantity of composition. The solutions of the active substance in organic solvents may be provided with a phytotoxicity-reducing substance, for example, wool fat, wool fatty acid or wool fatty alcohol.

A few forms of composition will be described in greater detail hereinafter by way of example.

Granular compositions are prepared by taking up, for example, the active substance in a solvent or dispersing it in a diluent and impregnating the resulting solution/suspension, if desired in the presence of a binder, on granular carrier material, for example porous granules (for example pumice and attaclay), mineral non-porous granules (sand or ground marl), organic granules (for example, dried coffee grounds, cut tobacco stems or ground corncobs). A granular composition can also be prepared by compressing the active substance together with powdered minerals in the presence of lubricants and binders and disintegrating the compressed product to the desired grain size and sieving it. Granular compositions can be prepared in a different manner by mixing the active substance in powder form with powdered fillers and then glomulating the mixture to the desired particle size.

Dusting powders can be obtained by intimately mixing the active substance with an inert solid powdered carrier material, for example, talcum.

Dispersible powders are prepared by mixing 10 to 80 parts by weigt of a solid inert carrier, for example kaolin, dolomite, gypsum, chalk, bentonite, attapulgite, colloidal $SiO_2$ or mixtures of these and similar substances, with 10 to 80 parts by weight of the active substance, 1 to 5 parts by weight of a dispersing agent, for example the lignine sulphonates or alkylnaphthalene sulphonates known for this purpose, preferably also 0.5 to 5 parts by weight of a wetting agent, for example, fatty alcohol sulphates, alkyl aryl sulphonates, fatty acid condensation products, or polyoxyethylene compounds, and finally other additives, if desired.

For the preparation of miscible oils the active compound is dissolved in a suitable solvent which preferably is poorly water-miscible, and one or more emulsifiers are added to this solution. Suitable solvents are, for example, higher alcohols, e.g. lauryl alcohol, decanol and octanol, further xylene, toluene, petroleum distillates which are rich in aromatics, for example, solvent naphtha, distilled tar oil and mixtures of these liquids. As emulsifiers may be used, for example, polyoxyethylene compounds and/or alkyl aryl sulphonates. The concentration of the active compound in these miscible oils is not restricted to narrow limits and may vary, for example, between 2 and 50% by weight.

In addition to a miscible oil may also be mentioned as a liquid and highly concentrated primary composition a solution of the active substance in a readily watermiscible liquid, for example, a glycol, a glycol ether or dimethyl formamide, to which solution a dispersing agent and, if desired, a surface-active substance has been added. When diluting with water shortly before or during spraying, an aqueous dispersion of the active substance is then obtained.

In addition to the above-mentioned ingredients, the agents according to the invention may also contain other substances known for use in this type of agents. For example, a lubricant, for example, calcium stearate or magnesium stearate, may be added to a dispersible powder or a mixture to be granulated. "Adhesives", for example, polyvinylalcohol cellulose derivatives or other colloidal materials, such as casein, may also be added so as to improve the adhesion of the composition to the plant. Furthermore, a substance may be added to reduce the phytotoxicity of the active substance, carrier material or auxiliary substance, for example, wool fat or wool fatty alcohol.

Plant growth regulating and/or pesticidal compounds known per se may also be incorporated in the compositions according to the invention. As a result of this the activity spectrum of the composition is widened and synergism may occur. In addition fertilizers may be added to the composition.

The following known plant growth regulating and/or herbicidal compounds and fungicidal compounds are to be considered for use in combination compositions, in addition to insecticidal and acaricidal compounds known per se.

Herbicides, for example:
1. phenoxy compounds, for example, (2,4-dichlorophenoxy)-acetic acid, 4-chloro-o-tolyloxyacetic acid, and 2-[4-(5-trifluoromethyl-2-pyridyloxy)phenoxy]-propionic acid butyl ester;
2. carboxylic acids, for example, 3-amino-2,5-dichlorobenzoic acid, 3,6-dichloro-2-methoxybenzoic acid and salts thereof, and N-1-naphthylphthaliminic acid and salts thereof;
3. nitro compounds and amides, for example, 2,6-dinitro-N,N-dipropyl-4-trifluoromethylaniline, N-(2-chloroethyl)-2,6-dinitro-N-propyl-4-trifluoromethylaniline, N-(1-ethylpropyl)-3,4-dimethyl-2,6-dinitroaniline, N-(3,4-dichlorophenyl)propionamide, 2-chloro-2',6'-diethyl-N-(methoxymethyl)acetanilide, and 2-chloro-N-(2,6-dimethylphenyl)-N-(1-H-pyrazol-1-ylmethyl)acetamide;
4. carbamates, for example, 1-isopropyl-3-chlorophenyl carbamate, S-ethyl diisobutylthiocarbamate, 1-(ethylcarbamoyl)ethylphenylcarbamate, 2,3-dichloroallyl diisopropylthiocarbamate, 2,3,3-trichloroallyl diisopropylthiocarbamate, methyl sulphanilylcarbamate, and S-(p-chlorobenzyl)diethylthiocarbamate;
5. heterocyclic nitrogen compounds, for example, 3-amino-1-H-1,2,4-triazole, 3,5,6-trichloro-2-pyridyloxyacetic acid, 4-amino-3,5,6-trichloropyridine-2-carboxylic acid, 1,2-dimethyl-3,5-diphenyl-1H-pyrazolium methyl sulphate, 5-amino-4-chloro-2-phenyl-3(2H)-pyridazinone, 4-chloro-5-(methylamino)-2[3-(trifluoromethyl)phenyl]-3(2H)-pyridazinone, 4,5-dimethoxy-2-phenyl-3-(2H)-pyridazinone, 3-chloro-4-chloromethyl-1-(3-trifluromethylphenyl)-2-pyrrolidone, 1-methyl-3-phenyl-5-[3-(trifluoromethyl)phenyl]-4-(1H)-pyridinone, sym. triazines (for example, 2-chloro-4-ethylamino-6-isopropylamino-1,3,5-triazine and 2-chloro-4-(1-cyano-1-methylethylamino)-6-ethylamino-1,3,5-trizine), sulphonyl urea compounds, (for example, 1-(2-chlorophenylsulphonyl)-3-(4-methoxy-6-methyl-1,3,5-triazin-2-yl)urea and 2-[3-(4,6-dimethylpyrimidin-2-yl)ureidosulphonyl]benzoic acid), and imidazolidones (for example, 2-(3-carboxyquinolyl)-5-isopropyl-5-methylimidazolidone-4);
6. urea compounds, for example, 3-(3,4-dichlorophenyl)-1,1-dimethylurea, 3-[4-(4-chlorophenoxy)-phenyl]-1,1-dimethylurea, 1,1-dimethyl-3-[3-(trifluoromethyl)phenyl]-urea, 3-(3-chloro-4-methylphenyl)-1,1-dimethylurea, 5-bromo-3-sec.-butyl-6-methyluracil, 1-benzothiazol-2-yl-1,3-dimethylurea, 3-(4-isopropylphenyl)-1,1-dimethylurea, and 3-(3-chloro-4-methoxyphenyl)-1,1-dimethylurea;
7. nitrophenyl ethers, for example, 2,4-dichlorophenyl 3-methoxy-4-nitrophenyl ether, 5-[2-chloro-4-(trifluoromethyl)phenoxy]-2-nitrobenzoic acid, 2-chloro-4-trifluoromethylphenyl 3-ethoxy-4-nitrophenyl ether, methyl 4-(2,4-dichlorophenoxy)-2-nitrobenzoate, ethyl 2-[{2-nitro-5-(2-chloro-4-trifluoromethylphenoxy)}phenylcabonyloxy]propionate and 2-chloro-4-trifluoromethylphenyl 3-methylsulphonylcarbamoyl-4-nitrophenyl ether;
8. nitriles, for example, 2,6-dichlorobenzonitrile, 3,5-dibromo-4-hydroxybenzonitrile and 4-hydroxy-3,5-diiodobenzonitrile;
and further:

ethyl 2(N-benzoyl-3,4-dichloroanilino)propionate, methyl N-benzoyl-N-(3-chloro-4-fluorophenyl)-2-aminopropionate, butyl 2-[4-(5-trifluoromethyl-2-pyridyloxy)phenoxy propionate, 2-(3,5-dichlorophenyl)-2-(2,2,2-trichloroethyl)oxirane, S-ethyl N,N-hexamethylene thiocarbamate, 5-tert.butyl-3-(2,4-dichloro-5-isopropoxyphenyl)-1,3,4-oxadiazol-2(3H)-one, N-(phosphonomethyl)glycine or salts thereof, methyl 2-[4-(2,4-dichlorophenoxy)phenoxy]-propionate, 3-isopropyl-(1H)-2,1,3-benzothiadiazin-4-(3H)-one 2,2-dioxide and 2-(1-ethoxyiminobutyl)-5-[2-(ethylthio) propyl]-3-hydroxycyclohex-2-enone.

Plant growth regulators, for example:
gibberellic acid, α-cyclopropyl-α-(4-methoxyphenyl)-5-pyrimidine methanol, 2-chloroethyltrimethylammonium salts, 2,3:4,6-di-O-isopropylidene-α-L-xylo-2-hexulofuranosonic acid sodium, 2-chloroethyl phosphonic acid, N,N-bis(phosphonomethyl)glycine, 1,1-dimethylpiperidinium chloride, N-[2,4-dimethyl-5-(trifluoromethylsulphonylamino)phenyl]-acetamide, maleic acid hydrazide, 2-(1-naphthyl) acetic acid, and fatty acids or lower esters thereof.

Fungicides, for example:
1. organic tin compounds, for example, triphenyltin hydroxide and triphenyltin acetate;
2. alkylene bisdithiocarbamates, for example, zinc ethylene bisdithiocarbamate and manganese ethylenebisdithiocarbamate;
3. 1-acyl- or 1-carbamoyl-N-benzimidazole(-2) carbamates and 1,2-bis(3-alkoxycarbonyl-2-thiureido)benzene, and furthermore, 2,4-dinitro-6-(1-methylheptylphenylcrotonate), 1-[bis(dimethylamino)phosphoryl]-3-phenyl-5-amino-1,2,4-triazole, N-trichloromethylthiophthalimide, N-trichloromethylthiotetrahydrophthalimide, N-(1,1,2,2-tetrachloroethylthio)tetrahydrophthalimide, N-dichlorofluoromethylthio-N-phenyl-N,N'-dimethylsulphamide, tetrachloroisophthalonitrile, 2-(4'-thiazolyl)-benzimidazole, 5-butyl-2-ethylamino-6-methylpyrimidin-4-yl-dimethylsulphamate, 1-(4-chlorophenoxy)-3,3-dimethyl-1(1,2,4-triazol-1-yl)-2-butanone, 1-[2-(2,4-dichlorophenyl)-4-propyl-1,3-dioxolan-2-ylmethyl]-1H-1,2,4-triazole, 2,4'-difluoro-α-(1H-1,2,4-triazol-1-ylmethyl)benzhydryl alcohol, α-(2-chlorophenyl)-α-(4-fluorophenyl)-5-pyrimidinemethanol, α-(2-chlorophenyl)-α-(4-chlorophenyl)-5-pyrimidinemethanol, 1-(isopropylcarbamoyl)-3-(3,5-dichlorophenyl)-hydantoin, N-(1,1,2,2-tetrachloroethylthio)-4-cyclohexene-1,2-carboximide, N-trichloromethylthio-4-cyclohexene-1,2-dicarboximide, N-tridecyl-2,6-dimethylmorpholine, 5,6-dihydro-2-methyl-1,4-oxathiine-3-carboxanilide, metal salts of ethyl phosphate, and N-(2,6-dimethylphenyl)-N-(methoxyacetyl)alanine methyl ester, or mixtures of these compounds.

The dosages of the composition according to the invention desired for practical application will, of course, depend on various factors, for example, field of application, selected active substance, form of composition, nature and size of the weeds and the crops, and the weather conditions.

In general it holds that favourable results can be achieved with a dosage which corresponds to from 0.01 to 10 kg of the active substance per hectare, preferable 0.1 to 3 kg per hectare.

It has been found that the herbicidal activity of the compositions according to the invention may increase considerably by the use of suitable adjuvants, for example, mineral oils and/or polyalcohols and/or polyoxyethylene compounds, for example, the mineral oils and surface-active substances mentioned in Netherlands Patent Application Ser. No. 7613453. The quantity of the adjuvant to be used may vary between wide limits dependent on the application and usually is between 10 and 10,000 ml per hectare.

The compounds according to the invention of the general formula I may be prepared by reacting a compound of the general formula

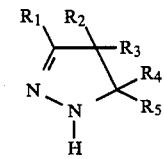

wherein
$R_1$, $R_2$, $R_3$, $R_4$ and $R_5$ have the meanings given hereinbefore, with a compound of the general formula

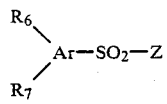

wherein
$R_6$, $R_7$ and Ar also have the meanings given hereinbefore,
and
Z is an isocyanato group, an ureido group, a phenoxycarbonylamino group, or a lower alkoxycarbonylamino group.

The reaction in which an 1-unsubstituted-2-pyrazoline is coupled with an arylsulphonylisocyanate, is preferably carried out in an inert organic solvent, for example, an aromatic hydrocarbon, e.g. toluene, or a chlorinated hydrocarbon, such as chloroform, methylene chloride or dichloroethane, preferably at room temperature or a slightly decreased temperature. The arylsulphonyl isocyanate to be used as the starting material can be prepared in a manner known per se for corresponding compounds, for example, by reacting the corresponding arylsulphonamide with chlorosulphonylisocyanate, preferably in a suitable organic solvent, for example, an aromatic hydrocarbon, at elevated temperature. The reaction between an 1-unsubstituted-2-pyrazoline and an arylsulphonylurea or arylsulphonylcarbamic ester is preferably carried out in an inert organic solvent, for example an ether, e.g. dioxane, if desired in the presence of an organic base, e.g. an amine, preferably at a temperature between room temperature and the boiling point of the solvent used. The starting sulphonylurea or sulphonylcarbamic ester can be prepared from the corresponding sulphonamide and an alkali metal cyanate or a chloroformate respectively in a usual manner. The arylsulphonamide may be prepared in a usual manner, for example, from arylsulphonylchloride and ammonia. The 2-pyrazoline to be used as the starting material may be prepared by reacting a suitable α,β-alkenone or -alkenal with hydrazine, optionally in the form of a hydrate, preferably in a polar organic solvent, for example, an alkanol, e.g. methanol, at a temperature between 0° C. and the boiling-point of the solvent.

Dependent on the substitution pattern at the pyrazoline ring, the new pyrazoline derivatives according to the invention may occur in stereoisomers, for example, the cis- and the transform. Of course, mixtures of these stereoisomers in all ratios are possible. Optionally, these stereoisomers may be separated from each other by technics known for this purpose, such as recrystallisation and/or column chromatography. The activity of the active substance may be influenced by the steric configuratin.

The 1-carbamoyl-2-pyrazolines according to the invention may form salts with inorganic bases, for example, sodium hydroxide, potassium hydroxide or calcium hydroxide, and with organic bases, for example, pyridine or amines like diethylamine, triethylamine, diethanolamine or triethanolamine. As a result of this the formulation to a herbicidal composition may be favoured and/or the absorption by the plant may be improved, which is in favour of the activity. It has further been found that the 1-carbamoyl-2-pyrazolines according to the invention in general dissolve rather easily in water or in aqueous mixtures, which also facilitates the formulation. Such aqueous solutions prove to be stable over a large pH range; even at a pH of 4 not any decomposition can be established.

The invention will now be described in greater detail with reference to the ensuing specific examples.

EXAMPLE I

Preparation of 1-(2,6-dichlorophenylsulphonylcarbamoyl)-3,5,5-trimethyl-2-pyrazoline (43).

(a) 1 l of concentrated hydrochloric acid is added to a solution of 162 g of 2,6-dichloroaniline in 200 ml of acetic acid and then, while stirring and cooling to below 10° C. (ice/acetone), a solution of 76 g of sodium nitrite in 120 ml of water is added. After stirring for one hour at the same temperature the reaction mixture is filtered and the filtrate is slowly poured into a mixture of 17.1 g of $CuCl_2.2H_2O$, 30 ml of conc. hydrochloric acid, 400 ml of acetic acid, 400 ml of toluene and 200 ml of liquid sulphur dioxide. After stirring for 1 hour, the toluene layer is separated, diluted with approx. 400 ml of toluene, washed two times with water, dried, filtered and evaporated. After stirring with 400 ml of petroleum ether (40–60), the residue provides the desired 2,6-dichlorobenzenesulphonylchloride as a crystalline product having a melting-point of 52°–55° C.; yield 178.6 g.

122.75 g of this sulphonylchloride are dissolved in 1 l of ethanol. To this solution 1 l of conc. ammonia is added while stirring, after which the reaction mixture is refluxed for 5 hours. After distilling off approx. 1 l of solvent, the desired 2,6-dichlorobenzenesulphonamide crystallises upon cooling the reaction mixture and can be sucked off, washed with water and dried. Yield 104.84 g; melting-point 174°–176° C. The substance can be further purified by dissolving in 2N sodium hydroxide solution, filtering the solution, again acidifying with dilute hydrochloric acid, sucking off, and washing and drying the precipitate. 62.0 g of chlorosulphonylisocyanate are added to a solution of 85.6 g of the pure sulphonamide and 1.9 g of DABCO (diazabicyclooctane) in 650 ml of chlorobenzene. The reaction mixture is stirred at approx. 100° C. for 3 hours. After cooling, decanting and evaporating, the resulting residue is distilled twice under reduced pressure. The desired 2,6-dichlorobenzenesulphonylisocyanate is obtained in a yield of 42.26 g; liquid; b.p. 106–119/50 Pa. (b) 198.7 g of 4-methylpenten-3-one-2 are added dropwise, while stirring and cooling (temperature below 30° C.) under nitrogen to a solution of 100.0 g of hydrazine hydrate in 100 ml of methanol. After stirring for 3 hours and leaving to stand overnight under nitrogen, the reaction mixture is distilled twice under reduced pressure. The desired 3,5,5-trimethyl-2-pyrazoline is obtained as a colourless liquid in a yield of 122.6 g; boiling-point 66°/69° C./3200 Pa.

(c) 11.2 g of the 3,5,5-trimethyl-2-pyrazoline obtained according to example I(b) are added dropwise while stirring, cooling in cold water and under a nitrogen blanket to a solution of 25.2 g of the 2,6-dichlorobenzenesulphonylisocyanate obtained according to example I(a) in 200 ml of dry toluene. After stirring at room temperature for two hours, the precipitate is sucked off and washed successively with dry toluene and petroleum ether (40-60). The desired 1-(2,6-dichlorophenylsulphonylcarbamoyl)-3,5,5-trimethyl-2-pyrazoline is obtained in a yield of 20.07 g; melting-point 270° C. (decomposition).

The following compounds are prepared in a corresponding manner; the numbers of the compounds correspond to the numbers used before in the specification.

| comp. no. | phys. characteristics |
|---|---|
| (1) | melt. p. 120° C. |
| (2) | melt. p. 157° C. |
| (3) | melt. p. 148° C. (decomp) |
| (4) | melt. p. 180° C. |
| (5) | melt. p. 150° C. (decomp) |
| (6) | melt. p. 138° C. |
| (7) | melt. p. 158° C. |
| (8) | melt. p. 118° C. |
| (9) | melt. p. 182° C. |
| (10) | melt. p. 187° C. |
| (11) | melt. p. 134° C. |
| (12) | melt. p. 115° C. |
| (13) | melt. p. 124° C. |
| (14) | melt. p. 147° C. |
| (15) | melt. p. 184° C. |
| (16) | melt. p. 127° C. |
| (17) | melt. p. 111° C. |
| (18) | melt. p. 130° C. |
| (19) | melt. p. 132° C. |
| (20) | melt. p. 150° C. (decomp) |
| (21) | oil; $R_f$(EtOAc) 0.20 |
| (22) | oil; $R_f$(EtOAc) 0.45 |
| (23) | oil; $R_f$(EtOAc) 0.43 |
| (24) | oil; $R_f$(EtOAc) 0.50 |
| (25) | oil; $R_f$(EtOAc) 0.35 |
| (26) | oil; $R_f$(EtOAc) 0.55 |
| (27) | melt. p. 120° C. |
| (28) | melt. p. 125° C. |
| (29) | melt. p. 152° C. |
| (31) | oil; $R_f$(EtOAc) 0.50 |
| (32) | oil; $R_f$(EtOAc) 0.52 |
| (33) | oil; $R_f$(EtOAc) 0.45 |
| (34) | oil; $R_f$(EtOAc) 0.48 |
| (35) | oil; $R_f$(EtOAc) 0.44 |
| (36) | oil; $R_f$(EtOAc) 0.48 |
| (37) | oil; $R_f$(EtOAc) 0.50 |
| (38) | oil; $R_f$(EtOAc) 0.42 |
| (39) | melt. p. 130° C. |
| (40) | melt. p. 165° C. |
| (41) | melt. p. 182° C. |
| (42) | melt. p. 195° C. (decomp) |
| (44) | melt. p. 197° C. (decomp) |
| (45) | melt. p. 255° C. |
| (46) | melt. p. 185° C. (decomp) |
| (47) | melt. p. 177° C. |
| (48) | melt. p. 153° C. |
| (49) | melt. p. 171° C. |
| (50) | melt. p. 129° C. |
| (51) | melt. p. 146° C. |
| (52) | melt. p. 145° C. |
| (53) | melt. p. 123° C. |
| (54) | melt. p. 170° C. |

| comp. no. | phys. characteristics |
|---|---|
| (55) | vitreous; R$_f$(EtOAc) 0.65 |
| (56) | melt. p. 221° C. |
| (57) | melt. p. 160° C. (decomp) |
| (58) | melt. p. 144° C. |
| (59) | melt. p. 155° C. |
| (60) | melt. p. 194° C. |
| (61) | melt. p. 178° C. |
| (62) | melt. p. 184° C. |
| (63) | melt. p. 142° C. |
| (64) | melt. p. 128° C. |
| (65) | melt. p. 86° C. |
| (66) | melt. p. 187° C. |
| (67) | melt. p. 140° C. |
| (68) | melt. p. 165° C. |
| (69) | melt. p. 153° C. |
| (70) | melt. p. 147° C. |
| (71) | melt. p. 152° C. |
| (72) | melt. p. 106° C. |
| (73) | melt. p. 131° C. |
| (74) | melt. p. 111° C. |
| (75) | oil; R$_f$(EtOAc) 0.48 |
| (76) | melt. p. 165° C. |
| (77) | melt. p. 143° C. |
| (78) | melt. p. 188° C. |
| (79) | melt. p. 185° C. |
| (80) | oil; R$_f$(EtOAc) 0.45 |
| (81) | melt. p. 144° C. |
| (82) | melt. p. 174° C. |
| (83) | melt. p. 100° C. |
| (84) | melt. p. 160° C. |
| (85) | melt. p. 127° C. |
| (86) | melt. p. 128° C. |
| (87) | melt. p. 84° C. |
| (88) | melt. p. 129° C. |
| (89) | oil; R$_f$(EtOAc) 0.40 |
| (90) | melt. p. 132° C. |
| (91) | melt. p. 125° C. |
| (92) | melt. p. 108° C. |
| (93) | melt. p. 146° C. |
| (94) | oil; R$_f$(EtOAc) 0.52 |
| (95) | melt. p. 65° C. |
| (96) | oil; R$_f$(EtOAc) 0.59 |
| (97) | oil; R$_f$(EtOAc) 0.48 |
| (98) | oil; R$_f$(EtOAc) 0.41 |
| (99) | oil; R$_f$(EtOAc) 0.43 |
| (100) | melt. p. 182° C. |
| (101) | oil; R$_f$(EtOAc) 0.39 |
| (102) | melt. p. 125° C. |
| (103) | melt. p. 124° C. |
| (104) | melt. p. 160° C. |
| (105) | melt. p. 162° C. |
| (106) | melt. p. 174° C. |
| (107) | oil; R$_f$(EtOAc) 0.50 |
| (108) | oil; R$_f$(EtOAc) 0.42 |
| (109) | oil; R$_f$(EtOAc) 0.40 |
| (110) | oil; R$_f$(EtOAc) 0.38 |
| (111) | melt. p. 128° C. |
| (112) | melt. p. 208° C. |
| (113) | melt. p. 177° C. |
| (114) | melt. p. 137° C. |
| (115) | melt. p. 162° C. |
| (116) | melt. p. 151° C. |
| (117) | melt. p. 212° C. |
| (118) | melt. p. 159° C. |
| (119) | melt. p. 147° C. |
| (120) | melt. p. 177° C. |
| (121) | melt. p. 143° C. |
| (122) | melt. p. 193° C. |
| (123) | melt. p. 148° C. |
| (124) | melt. p. 120° C. |
| (125) | melt. p. 196° C. |
| (126) | melt. p. 153° C. |
| (127) | melt. p. 182° C. |
| (128) | melt. p. 161° C. |
| (129) | melt. p. 171° C. |
| (130) | melt. p. 191° C. |
| (131) | melt. p. 175° C. |
| (132) | melt. p. 177° C. |
| (133) | melt. p. 137° C. |
| (134) | melt. p. 158° C. |
| (135) | melt. p. 184° C. |
| (136) | oil; R$_f$(EtOAc) 0.30 |
| (137) | melt. p. 164° C. |
| (138) | oil; R$_f$(EtOAc) 0.43 |
| (139) | oil; R$_f$(EtOAc) 0.40 |
| (140) | melt. p. 158° C. |
| (141) | oil; R$_f$(EtOAc) 0.39 |
| (142) | melt. p. 165° C. |
| (143) | melt. p. 228° C. |
| (144) | melt. p. 265° C. |
| (145) | melt. p. 285° C. |
| (146) | oil; R$_f$(EtOAc) 0.30 |
| (147) | melt. p. 174° C. |
| (148) | melt. p. 178° C. |
| (149) | oil; R$_f$(EtOAc) 0.50 |
| (150) | melt. p. 127° C. |
| (151) | melt. p. 138° C. |
| (152) | oil; R$_f$(EtOAc) 0.41 |
| (153) | oil; R$_f$(EtOAc) 0.32 |
| (154) | melt. p. 108° C. |
| (155) | melt. p. 140° C. |
| (156) | oil; R$_f$(EtOAc) 0.53 |
| (157) | melt. p. 178° C. |
| (158) | melt. p. 178° C. |
| (159) | oil; R$_f$(EtOAc) 0.55 |
| (160) | oil; R$_f$(EtOEt) 0.60 |
| (162) | melt. p. 139° C. |
| (163) | melt. p. 134° C. |
| (164) | melt. p. 120° C. |
| (165) | melt. p. 127° C. |
| (166) | melt. p. 135° C. |
| (167) | melt. p. 163° C. |
| (168) | melt. p. 123° C. |
| (169) | melt. p. 171° C. |
| (170) | melt. p. 162° C. |
| (171) | melt. p. 164° C. |
| (172) | melt. p. 145° C. |
| (173) | melt. p. 138° C. |
| (174) | melt. p. 187° C. |
| (175) | melt. p. 164° C. |
| (176) | melt. p. 150° C. |
| (177) | melt. p. 128° C. |
| (178) | melt. p. 171° C. |
| (179) | melt. p. 148° C. |
| (180) | melt. p. 113° C. |
| (181) | melt. p. 127° C. |
| (182) | melt. p. 128° C. |
| (183) | melt. p. 156° C. |
| (184) | melt. p. 118° C. |
| (185) | melt. p. 140° C. |
| (186) | vitreous; R$_f$(EtOAc) 0.55 |
| (187) | melt. p. 89° C. |
| (188) | oil; R$_f$(EtOAc) 0.42 |
| (189) | oil; R$_f$(EtOAc) 0.39 |
| (190) | vitreous; R$_f$(EtOAc) 0.23 |
| (191) | vitreous; R$_f$(EtOAc) 0.12 |
| (192) | vitreous; R$_f$(EtOAc) 0.17 |
| (193) | vitreous; R$_f$(EtOAc) 0.24 |
| (194) | vitreous; R$_f$(EtOAc) 0.13 |

EXAMPLE II

Preparation of 1-(2,6-difluorophenylsulphonylcarbamoyl)-3-methyl-2-pyrazoline (161).

(a) To a solution of 19.3 g of 2,6-difluorophenylsulphonylamide in 100 ml of acetonitrile, containing 35 ml of triethylamine is added dropwise while stirring 7.7 ml of methylchloroformate; temperature maintained by external cooling on 15°-20° C. Then the reaction mixture is stirred for 3 hours at room temperature. The solvent is removed at reduced pressure, the remaining solid is dissolved in 100 ml of water and the obtained solution filtered and acidified with 25 ml of conc. hydrochloric acid. The desired N-(2,6-difluorophenylsulphonyl)-methylcarbamate is obtained in a yield of 20.8 g; melting point 148° C.

(b) A mixture of 2.51 g of N-(2,6-difluorophenylsulphonyl)methylcarbamate, 1.68 g of 3-methyl-2-pyrazoline and 3 ml of pyridine in 20 ml of dioxane is heated on a steambath for 2 hours. After cooling the solvent is evaporated under reduced pressure and the residue is dissolved in 20 ml of water. This solution is filtrated and then acidified with conc. hydrochloric acid. The title compound, viz. 1-(2,6-difluorophenylsulphonylcarbamoyl)-3-methyl-2-pyrazoline, is obtained in a yield of 2.50 g; melting point 196° C.

If instead of pyridine other organic bases like triethylamine are used, the same results are obtained.

In a corresponding manner the following compounds are prepared; the numbers of the compounds correspond to the number used before in the specification.

| comp. no. | melting point | yield (%) |
|---|---|---|
| (2) | 156° C. | 74 |
| (7) | 157° C. | 84 |
| (27) | 120° C. | 57 |
| (48) | 154° C. | 55 |
| (49) | 172° C. | 57 |
| (85) | 128° C. | 62 |

Starting substance for the above compounds (2), (27), (49) and (85) is conveniently prepared by preparing N-(methoxycarbonyl)saccharine from saccharine sodium and methylchloroformate, e.g. in refluxing acetonitrile, and converting the saccharine derivative to N-(methoxycarbonylphenylsulphonyl)-methylcarbamate with sodium methoxide in methanol: melting point 148° C.

EXAMPLE III

Preparation of 1-(2,6-difluorophenylsulphonylcarbamoyl)-2-pyrazoline (30).

(a) 2,6-Difluorophenylsulphonylamide in an amount of 9.65 g and 6.5 g of potassium cyanate in 100 ml of ethanol are refluxed for 3 hours. After dilution with water and filtration while hot the solution is acidified with 5 ml of conc. hydrochloric acid. The desired N-(2,6-difluorophenylsulphonyl)urea is obtained in a yield of 10.0 g; melting point 198° C. (decomp.)

(b) N-(2,6-difluorophenylsulphonyl)urea in an amount of 2.36 and 1.40 g of 2-pyrazoline in 20 ml of dioxane are refluxed for 4 hours. After evaporation of the solvent at reduced pressure, the remaining solid is dissolved in 20 ml of water. This solution is filtrated and acidified with conc. hydrochloric acid. The precipitate is sucked off, washed with water and dried, yielding the title product, viz. 1-(2,6-difluorophenylsulphonylcarbamoyl)-2-pyrazoline in a yield of 1.87 g; melting point 183° C.

In a corresponding manner compound no. (63) is prepared in a yield of 65%; melting point 142° C.

EXAMPLE IV (a) Preparation of a solution of an active substance, viz. 1-(2-methoxycarbonylphenylsulphonylcarbamoyl)-2-pyrazoline (2) in a water-miscible liquid ("liquid").

10 g of the above active solid are dissolved in a mixture of 10 ml of isophorone and approx. 70 ml of dimethylformamide, after which polyoxyethyleneglycol ricinyl ether is added as an emulsifier in a quantity of 10 g.

The other active substances are processed in a corresponding manner to 10% or 20% "liquids".

In a corresponding manner "liquids[ are obtained in N-methylpyrrolidone and isophorone as solvents.

(b) Preparation of a solution of the active substance in an organic solvent.

10 g of the active substance to be investigated are dissolved in 1,000 ml of acetone in the presence of 1.67 g of an emulsifier mixture consisting of an alkylarylsulphonate mixture and nonylphenolpolyoxyethylene. This solution, after diluting to the desired concentration, is used as a spray liquid.

(c) Preparation of an emulsifiable concentrate of the active substance.

10 g of the active substance to be investigated are dissolved in a mixture of 15 ml of isophorone and 70 ml of xylene; 5 g of a mixture of a polyoxyethylene sorbitan ester and an alkylbenzene sulphonate as an emulsifier are added to this solution.

(d) Preparation of a dispersible powder (W. P.) of the active substance.

25 g of the active substance to be investigated are mixed with 68 g of kaolin in the presence of 2 g of sodium butylnaphthalene sulphonate and 5 g of lignine sulphonate.

(e) Preparation of a suspension concentrate (flowable) of the active substance.

A mixture of 10 g of active substance, 2 g of lignine sulphonate and 0.8 g of a sodium alkyl sulphate is replenished with water, to a total quantity of 100 ml.

(f) Preparation of a granule of the active substance.

7.5 g of active substance, 5 g of sulphite lye and 87.5 of ground dolomite are mixed, after which the resulting mixture is processed to a granular composition by means of the so-called compacting method.

EXAMPLE V

Control of weeds (post-emergence) in the glasshouse.

Compounds according to the invention are used in a quantity of 1 kg per hectare against the following weeds: *Galinsoga parviflora* (small-flowered g., Gp), *Datura stramonium* (jimsonweed, Ds), *Chenopodium album* (common lambsquarters, Ca) and *Polygonum convolvulus* (wild buckwheat, Pc). Moreover, the following crops are present: *Triticum aestivum* (wheat, Ta) *Zea mays* (maize, Zm), and *Gossipum hirsutum* (cotton, Gh). After emergence the weeds and the crops are sprayed with a spray liquid obtained according to example IV(b) by means of a suitable spraying device. After 3 weeks the herbicidal activity is evaluated. The damage to the plants in percentage is recorded in Table A below.

TABLE A

| comp. no. | percentage damage to | | | | | | |
|---|---|---|---|---|---|---|---|
| | Ca | Ds | Gp | Pc | Ta | Zm | Gh |
| (1) | ca. 70 | ca. 70 | 90–100 | ca. 70 | ca. 30 | ca. 30 | 0–10 |
| (2) | 90–100 | ca. 70 | 90–100 | 90–100 | 0–10 | ca. 30 | ca. 30 |

TABLE A-continued

| | percentage damage to | | | | | | |
|---|---|---|---|---|---|---|---|
| comp. no. | Ca | Ds | Gp | Pc | Ta | Zm | Gh |
| (3) | ca. 70 | ca. 70 | ca. 70 | ca. 70 | 0-10 | 0-10 | 0-10 |
| (6) | ca. 70 | ca. 70 | ca. 70 | 90-100 | 0-10 | 0-10 | 0-10 |
| (7) | ca 70 | 90-100 | 90-100 | 90-100 | 0-10 | 0-10 | 0-10 |
| (8) | 90-100 | ca. 70 | 90-100 | 90-100 | 0-10 | ca. 30 | 0-10 |
| (9) | ca. 70 | ca. 70 | ca. 70 | ca. 70 | 0-10 | 0-10 | 0-10 |
| (10) | ca. 70 | ca. 70 | ca. 70 | ca. 70 | 0-10 | 0-10 | 0-10 |
| (11) | ca. 70 | ca. 70 | ca. 70 | 90-100 | 0-10 | 0-10 | 0-10 |
| (12) | ca. 70 | ca. 70 | ca. 70 | 90-100 | 0-10 | ca. 30 | ca. 30 |
| (14) | ca. 70 | ca. 70 | ca. 70 | 90-100 | 0-10 | 0-10 | 0-10 |
| (15) | ca. 70 | ca. 70 | ca. 70 | 90-100 | 0-10 | 0-10 | ca. 30 |
| (16) | ca. 70 | ca. 70 | 90-100 | 90-100 | ca. 30 | 0-10 | 0-10 |
| (18) | ca. 70 | ca. 70 | ca. 70 | ca. 70 | 0-10 | 0-10 | 0-10 |
| (19) | ca. 70 | ca. 70 | ca. 70 | ca. 70 | ca. 30 | 0-10 | 0-10 |
| (22) | 90-100 | ca. 70 | 90-100 | ca. 70 | 0-10 | 0-10 | 0-10 |
| (24) | 90-100 | ca. 70 | ca. 70 | ca. 70 | 0-10 | 0-10 | ca. 30 |
| (25) | ca. 70 | ca. 70 | ca. 70 | 90-100 | 0-10 | 0-10 | 0-10 |
| (26) | ca. 70 | ca. 70 | ca. 70 | ca. 70 | 0-10 | 0-10 | 0-10 |
| (28) | ca. 70 | ca. 70 | ca. 70 | ca. 70 | 0-10 | 0-10 | 0-10 |
| (29) | ca. 70 | ca. 70 | 90-100 | ca. 70 | 0-10 | 0-10 | 0-10 |
| (32) | ca. 70 | ca. 70 | ca. 70 | 90-100 | 0-10 | 0-10 | 0-10 |
| (33) | 90-100 | ca. 70 | 90-100 | ca. 70 | ca. 30 | 0-10 | ca. 30 |
| (38) | 90-100 | ca. 70 | 90-100 | 90-100 | 0-10 | 0-10 | ca. 30 |
| (39) | ca. 70 | ca. 70 | ca. 70 | ca. 70 | 0-10 | 0-10 | 0-10 |
| (40) | ca. 70 | ca. 70 | 90-100 | ca. 70 | 0-10 | 0-10 | 0-10 |
| (41) | 90-100 | ca. 70 | ca. 70 | ca. 70 | 0-10 | 0-10 | ca. 30 |
| (42) | 90-100 | ca. 70 | 90-100 | ca. 70 | 0-10 | 0-10 | 0-10 |
| (43) | ca. 70 | ca. 70 | 90-100 | ca. 70 | 0-10 | 0-10 | ca. 30 |
| (44) | 90-100 | ca. 70 | 90-100 | ca. 70 | 0-10 | 0-10 | ca. 30 |
| (45) | 90-100 | ca. 70 | ca. 70 | ca. 70 | 0-10 | 0-10 | ca. 30 |
| (51) | 90-100 | ca. 70 | 90-100 | 90-100 | 0-10 | 0-10 | 0-10 |
| (52) | ca. 70 | ca. 70 | 90-100 | ca. 70 | 0-10 | 0-10 | 0-10 |
| (53) | ca. 70 | ca. 70 | 90-100 | ca. 70 | 0-10 | 0-10 | 0-10 |
| (54) | 90-100 | ca. 70 | ca. 70 | 90-100 | 0-10 | 0-10 | ca. 30 |
| (56) | 90-100 | ca. 70 | 90-100 | 90-100 | 0-10 | 0-10 | 0-10 |
| (57) | 90-100 | ca. 70 | 90-100 | ca. 70 | 0-10 | 0-10 | 0-10 |
| (64) | ca. 70 | ca. 70 | ca. 70 | ca. 70 | 0-10 | 0-10 | 0-10 |
| (65) | ca. 70 | ca. 70 | ca. 70 | ca. 70 | 0-10 | 0-10 | ca. 30 |
| (66) | ca. 70 | ca. 70 | ca. 70 | 90-100 | 0-10 | 0-10 | 0-10 |
| (67) | ca. 70 | ca. 70 | ca. 70 | ca. 70 | 0-10 | 0-10 | 0-10 |
| (68) | ca. 70 | ca. 70 | ca. 70 | ca. 70 | 0-10 | 0-10 | ca. 30 |
| (69) | ca. 70 | ca. 70 | ca. 70 | ca. 70 | 0-10 | 0-10 | 0-10 |
| (70) | ca. 70 | 90-100 | ca. 70 | 90-100 | ca. 30 | 0-10 | 0-10 |
| (71) | ca. 70 | ca. 70 | ca. 70 | ca. 70 | 0-10 | 0-10 | ca. 30 |
| (72) | ca. 70 | ca. 70 | ca. 70 | ca. 70 | 0-10 | 0-10 | 0-10 |
| (73) | ca. 70 | ca. 70 | ca. 70 | ca. 70 | 0-10 | 0-10 | 0-10 |
| (74) | ca. 70 | ca. 70 | ca. 70 | ca. 70 | ca. 30 | 0-10 | ca. 30 |
| (75) | ca. 70 | ca. 70 | 90-100 | ca. 70 | 0-10 | 0-10 | 0-10 |
| (76) | ca. 70 | ca. 70 | 90-100 | 90-100 | 0-10 | 0-10 | 0-10 |
| (77) | ca. 70 | ca. 70 | 90-100 | 90-100 | 0-10 | 0-10 | 0-10 |
| (78) | 90-100 | ca. 70 | 90-100 | 90-100 | 0-10 | 0-10 | ca. 30 |
| (79) | ca. 70 | ca. 70 | ca. 70 | ca. 70 | 0-10 | 0-10 | 0-10 |
| (80) | ca. 70 | ca. 70 | ca. 70 | ca. 70 | 0-10 | 0-10 | 0-10 |
| (81) | ca. 70 | ca. 70 | 90-100 | ca. 70 | 0-10 | 0-10 | ca. 30 |
| (82) | ca. 70 | ca. 70 | ca. 70 | ca. 70 | 0-10 | 0-10 | 0-10 |
| (83) | ca. 70 | ca. 70 | ca. 70 | ca. 70 | ca. 30 | 0-10 | ca. 30 |
| (89) | ca. 70 | ca. 70 | ca. 70 | ca. 70 | 0-10 | 0-10 | ca. 30 |
| (90) | ca. 70 | ca. 70 | ca. 70 | ca. 70 | 0-10 | 0-10 | ca. 30 |
| (91) | ca. 70 | ca. 70 | ca. 70 | 90-100 | 0-10 | 0-10 | ca. 30 |
| (92) | ca. 70 | ca. 70 | 90-100 | ca. 70 | ca. 30 | 0-10 | ca. 30 |
| (93) | ca. 70 | ca. 70 | ca. 70 | ca. 70 | 0-10 | 0-10 | 0-10 |
| (94) | 90-100 | ca. 70 | ca. 70 | 90-100 | 0-10 | 0-10 | 0-10 |
| (95) | ca. 70 | ca. 70 | ca. 70 | ca. 70 | 0-10 | ca. 30 | ca. 30 |
| (96) | ca. 70 | ca. 70 | ca. 70 | ca. 70 | 0-10 | 0-10 | ca. 30 |
| (97) | ca. 70 | ca. 70 | ca. 70 | ca. 70 | 0-10 | 0-10 | ca. 30 |
| (99) | ca. 70 | ca. 70 | ca. 70 | 90-100 | 0-10 | 0-10 | 0-10 |
| (100) | ca. 70 | ca. 70 | ca. 70 | ca. 70 | 0-10 | 0-10 | 0-10 |
| (102) | ca. 70 | ca. 70 | ca. 70 | ca. 70 | 0-10 | 0-10 | ca. 30 |
| (103) | ca. 70 | ca. 70 | ca. 70 | ca. 70 | 0-10 | 0-10 | ca. 30 |
| (105) | ca. 70 | ca. 70 | ca. 70 | ca. 70 | 0-10 | 0-10 | 0-10 |
| (106) | ca. 70 | ca. 70 | 90-100 | 90-100 | 0-10 | 0-10 | ca. 30 |
| (107) | ca. 70 | ca. 70 | ca. 70 | ca. 70 | 0-10 | 0-10 | ca. 30 |
| (108) | ca. 70 | ca. 70 | ca. 70 | ca. 70 | 0-10 | 0-10 | ca. 30 |
| (109) | ca. 70 | ca. 70 | ca. 70 | ca. 70 | 0-10 | 0-10 | 0-10 |
| (110) | ca. 70 | ca. 70 | ca. 70 | ca. 70 | ca. 30 | 0-10 | 0-10 |
| (111) | ca. 70 | ca. 70 | 90-100 | ca. 70 | 0-10 | 0-10 | 0-10 |
| (112) | ca. 70 | ca. 70 | ca. 70 | ca. 70 | 0-10 | 0-10 | 0-10 |
| (113) | ca. 70 | 90-100 | 90-100 | ca. 70 | 0-10 | 0-10 | ca. 30 |
| (114) | ca. 70 | ca. 70 | ca. 70 | ca. 70 | ca. 30 | 0-10 | ca. 30 |
| (115) | 90-100 | ca. 70 | 90-100 | 90-100 | 0-10 | 0-10 | 0-10 |
| (116) | ca. 70 | ca. 70 | ca. 70 | ca. 70 | 0-10 | 0-10 | 0-10 |

TABLE A-continued

| comp. no. | Ca | Ds | Gp | Pc | Ta | Zm | Gh |
|---|---|---|---|---|---|---|---|
| (117) | ca. 70 | ca. 70 | ca. 70 | 90–100 | 0–10 | 0–10 | ca. 30 |
| (118) | ca. 70 | ca. 70 | ca. 70 | ca. 70 | 0–10 | 0–10 | 0–10 |
| (119) | ca. 70 | 90–100 | 90–100 | 90–100 | ca. 30 | ca. 30 | 0–10 |
| (120) | ca. 70 | ca. 70 | ca. 70 | ca. 70 | ca. 30 | 0–10 | 0–10 |
| (121) | ca. 70 | ca. 70 | ca. 70 | ca. 70 | 0–10 | 0–10 | 0–10 |
| (122) | ca. 70 | ca. 70 | ca. 70 | ca. 70 | 0–10 | 0–10 | 0–10 |
| (123) | ca. 70 | ca. 70 | ca. 70 | ca. 70 | ca. 30 | ca. 30 | 0–10 |
| (124) | ca. 70 | ca. 70 | ca. 70 | ca. 70 | 0–10 | 0–10 | 0–10 |
| (126) | 90–100 | ca. 70 | 90–100 | ca. 70 | 0–10 | 0–10 | ca. 30 |
| (128) | ca. 70 | ca. 70 | 90–100 | ca. 70 | 0–10 | ca. 30 | ca. 30 |
| (129) | ca. 70 | ca. 70 | 90–100 | ca. 70 | 0–10 | ca. 30 | ca. 30 |
| (134) | ca. 70 | ca. 70 | ca. 70 | ca. 70 | 0–10 | 0–10 | 0–10 |
| (135) | ca. 70 | ca. 70 | ca. 70 | ca. 70 | 0–10 | 0–10 | 0–10 |
| (136) | ca. 70 | ca. 70 | ca. 70 | 90–100 | 0–10 | 0–10 | ca. 30 |
| (137) | ca. 70 | ca. 70 | ca. 70 | ca. 70 | 0–10 | 0–10 | ca. 30 |
| (138) | ca. 70 | ca. 70 | ca. 70 | ca. 70 | 0–10 | 0–10 | ca. 30 |
| (140) | ca. 70 | ca. 70 | ca. 70 | ca. 70 | ca. 30 | 0–10 | 0–10 |
| (141) | ca. 70 | ca. 70 | 90–100 | ca. 70 | ca. 30 | 0–10 | ca. 30 |
| (142) | ca. 70 | ca. 70 | 90–100 | ca. 70 | ca. 30 | 0–10 | ca. 30 |
| (144) | ca. 70 | ca. 70 | ca. 70 | ca. 70 | 0–10 | 0–10 | 0–10 |
| (147) | ca. 70 | ca. 70 | ca. 70 | ca. 70 | 0–10 | 0–10 | 0–10 |
| (156) | 90–100 | ca. 70 | 90–100 | 90–100 | 0–10 | 0–10 | ca. 30 |
| (157) | 90–100 | ca. 70 | 90–100 | 90–100 | 0–10 | 0–10 | ca. 30 |
| (159) | ca. 70 | ca. 70 | 90–100 | ca. 70 | 0–10 | 0–10 | 0–10 |

EXAMPLE VI

Control of weeds (post-emergence) in the glasshouse.

Compounds according to the invention are used against the following weeds in quantities of 1,000 and 300 g per hectare in the same manner as indicated in Example V: *Galinsoga parviflora* (small-flowered g., Gp), *Datura stramonium* (jimsonweed, Ds), *Chenopodium album* (common lambsquarters, Ca), *Polygonum convolvulus* (wild buckwheat, Pc) and *Galium aparine* (cleavers, Ga.) The results are recorded in Table B below.

TABLE B

| compound no. | quantity (g/ha) | Ca | Ds | Ga | Gp | Pc |
|---|---|---|---|---|---|---|
| (1) | 1000 | ca. 70 | ca. 70 | 90–100 | 90–100 | ca. 70 |
|  | 300 | ca. 70 | ca. 70 | ca. 70 | ca. 70 | ca. 70 |
| (2) | 1000 | 90–100 | ca. 70 | ca. 70 | ca. 70 | 90–100 |
|  | 300 | 90–100 | ca. 70 | ca. 70 | ca. 70 | 90–100 |
| (7) | 1000 | ca. 70 | 90–100 | 90–100 | 90–100 | 90–100 |
|  | 300 | ca. 70 | ca. 70 | ca. 70 | ca. 70 | 90–100 |
| (8) | 1000 | 90–100 | ca. 70 | 90–100 | 90–100 | 90–100 |
|  | 300 | 90–100 | ca. 70 | 90–100 | ca. 70 | 90–100 |
| (12) | 1000 | ca. 70 | ca. 70 | 90–100 | ca. 70 | 90–100 |
|  | 300 | ca. 70 | ca. 70 | ca. 70 | ca. 70 | 90–100 |
| (13) | 1000 | 90–100 | 90–100 | ca. 70 | ca. 70 | 90–100 |
|  | 300 | 90–100 | ca. 70 | ca. 70 | ca. 70 | ca. 70 |
| (14) | 1000 | ca. 70 | ca. 70 | 90–100 | ca. 70 | 90–100 |
|  | 300 | ca. 70 | ca. 70 | ca. 70 | ca. 70 | 90–100 |
| (15) | 1000 | ca. 70 | ca. 70 | ca. 70 | 90–100 | 90–100 |
|  | 300 | ca. 70 | ca. 70 | ca. 70 | 90–100 | 90–100 |
| (16) | 1000 | ca. 70 | ca. 70 | ca. 70 | 90–100 | 90–100 |
|  | 300 | ca. 70 | ca. 70 | ca. 70 | ca. 70 | ca. 70 |
| (17) | 1000 | ca. 70 | ca. 70 | 90–100 | ca. 70 | 90–100 |
|  | 300 | ca. 70 | ca. 70 | 90–100 | ca. 70 | ca. 70 |
| (23) | 1000 | 90–100 | ca. 70 | ca. 70 | 90–100 | 90–100 |
|  | 300 | 90–100 | ca. 70 | ca. 70 | 90–100 | 90–100 |
| (27) | 1000 | 90–100 | 90–100 | 90–100 | 90–100 | 90–100 |
|  | 300 | ca. 70 | ca. 70 | ca. 70 | 90–100 | 90–100 |
| (31) | 1000 | 90–100 | ca. 70 | 90–100 | 90–100 | 90–100 |
|  | 300 | ca. 70 | ca. 70 | 90–100 | 90–100 | 90–100 |
| (33) | 1000 | 90–100 | ca. 70 | 90–100 | 90–100 | ca. 70 |
|  | 300 | ca. 70 | ca. 70 | 90–100 | 90–100 | ca. 70 |
| (34) | 1000 | 90–100 | ca. 70 | 90–100 | 90–100 | ca. 70 |
|  | 300 | 90–100 | ca. 70 | 90–100 | 90–100 | ca. 70 |
| (35) | 1000 | 90–100 | ca. 70 | 90–100 | 90–100 | 90–100 |
|  | 300 | 90–100 | ca. 70 | 90–100 | 90–100 | 90–100 |
| (36) | 1000 | 90–100 | ca. 70 | ca. 70 | 90–100 | 90–100 |
|  | 300 | ca. 70 | ca. 70 | ca. 70 | 90–100 | 90–100 |
| (37) | 1000 | 90–100 | ca. 70 | ca. 70 | 90–100 | 90–100 |
|  | 300 | 90–100 | ca. 70 | ca. 70 | 90–100 | ca. 70 |
| (41) | 1000 | 90–100 | ca. 70 | ca. 70 | ca. 70 | ca. 70 |
|  | 300 | 90–100 | ca. 70 | ca. 70 | ca. 70 | ca. 70 |
| (42) | 1000 | 90–100 | ca. 70 | ca. 70 | 90–100 | ca. 70 |
|  | 300 | 90–100 | ca. 70 | ca. 70 | ca. 70 | ca. 70 |
| (43) | 1000 | ca. 70 | ca. 70 | ca. 70 | 90–100 | ca. 70 |
|  | 300 | ca. 70 | ca. 70 | ca. 70 | 90–100 | ca. 70 |
| (44) | 1000 | 90–100 | ca. 70 | ca. 70 | 90–100 | ca. 70 |
|  | 300 | 90–100 | ca. 70 | ca. 70 | ca. 70 | ca. 70 |
| (47) | 1000 | 90–100 | ca. 70 | ca. 70 | 90–100 | 90–100 |
|  | 300 | 90–100 | ca. 70 | ca. 70 | 90–100 | ca. 70 |
| (48) | 1000 | ca. 70 | 90–100 | ca. 70 | 90–100 | ca. 70 |
|  | 300 | ca. 70 | ca. 70 | ca. 70 | 90–100 | ca. 70 |
| (49) | 1000 | 90–100 | 90–100 | ca. 70 | ca. 70 | ca. 70 |
|  | 300 | ca. 70 | ca. 70 | ca. 70 | ca. 70 | ca. 70 |
| (50) | 1000 | 90–100 | 90–100 | ca. 70 | 90–100 | 90–100 |
|  | 300 | 90–100 | ca. 70 | ca. 70 | 90–100 | 90–100 |
| (58) | 1000 | 90–100 | ca. 70 | ca. 70 | ca. 70 | 90–100 |
|  | 300 | 90–100 | ca. 70 | ca. 70 | ca. 70 | 90–100 |
| (70) | 1000 | ca. 70 | 90–100 | ca. 70 | ca. 70 | 90–100 |
|  | 300 | ca. 70 | ca. 70 | ca. 70 | ca. 70 | ca. 70 |
| (76) | 1000 | ca. 70 | ca. 70 | ca. 70 | 90–100 | 90–100 |
|  | 300 | ca. 70 | ca. 70 | ca. 70 | ca. 70 | ca. 70 |
| (77) | 1000 | ca. 70 | ca. 70 | ca. 70 | 90–100 | 90–100 |
|  | 300 | ca. 70 | ca. 70 | ca. 70 | 90–100 | ca. 70 |
| (78) | 1000 | 90–100 | ca. 70 | ca. 70 | 90–100 | 90–100 |
|  | 300 | ca. 70 | ca. 70 | ca. 70 | ca. 70 | ca. 70 |
| (84) | 1000 | 90–100 | ca. 70 | ca. 70 | ca. 70 | 90–100 |
|  | 300 | ca. 70 | ca. 70 | ca. 70 | ca. 70 | ca. 70 |
| (85) | 1000 | 90–100 | 90–100 | 90–100 | 90–100 | 90–100 |
|  | 300 | 90–100 | 90–100 | 90–100 | ca. 70 | 90–100 |
| (86) | 1000 | 90–100 | ca. 70 | ca. 70 | 90–100 | 90–100 |
|  | 300 | 90–100 | ca. 70 | ca. 70 | ca. 70 | 90–100 |
| (87) | 1000 | 90–100 | ca. 70 | ca. 70 | 90–100 | 90–100 |
|  | 300 | ca. 70 | ca. 70 | ca. 70 | 90–100 | 90–100 |
| (94) | 1000 | 90–100 | ca. 70 | ca. 70 | ca. 70 | 90–100 |
|  | 300 | 90–100 | ca. 70 | ca. 70 | ca. 70 | ca. 70 |
| (98) | 1000 | ca. 70 | ca. 70 | ca. 70 | 90–100 | ca. 70 |
|  | 300 | ca. 70 | ca. 70 | ca. 70 | ca. 70 | ca. 70 |
| (101) | 1000 | 90–100 | ca. 70 | ca. 70 | ca. 70 | ca. 70 |
|  | 300 | ca. 70 | ca. 70 | ca. 70 | ca. 70 | ca. 70 |
| (104) | 1000 | ca. 70 | 90–100 | ca. 70 | ca. 70 | ca. 70 |
|  | 300 | ca. 70 | ca. 70 | ca. 70 | ca. 70 | ca. 70 |
| (106) | 1000 | ca. 70 | ca. 70 | ca. 70 | 90–100 | 90–100 |

TABLE B-continued

| compound no. | quantity (g/ha) | percentage damage to Ca | Ds | Ga | Gp | Pc |
|---|---|---|---|---|---|---|
| | 300 | ca. 70 | ca. 70 | ca. 70 | 90-100 | ca. 70 |
| (113) | 1000 | ca. 70 | 90-100 | 90-100 | 90-100 | ca. 70 |
| | 300 | ca. 70 | ca. 70 | ca. 70 | 90-100 | ca. 70 |
| (115) | 1000 | 90-100 | ca. 70 | ca. 70 | 90-100 | 90-100 |
| | 300 | ca. 70 | ca. 70 | ca. 70 | ca. 70 | ca. 70 |
| (125) | 1000 | ca. 70 | ca. 70 | ca. 70 | 90-100 | 90-100 |
| | 300 | ca. 70 | ca. 70 | ca. 70 | 90-100 | 90-100 |
| (126) | 1000 | 90-100 | ca. 70 | ca. 70 | 90-100 | ca. 70 |
| | 300 | ca. 70 | ca. 70 | ca. 70 | 90-100 | ca. 70 |
| (127) | 1000 | ca. 70 | 90-100 | ca. 70 | 90-100 | ca. 70 |
| | 300 | ca. 70 | ca. 70 | ca. 70 | 90-100 | ca. 70 |
| (128) | 1000 | ca. 70 | 90-100 | ca. 70 | 90-100 | ca. 70 |
| | 300 | ca. 70 | ca. 70 | ca. 70 | 90-100 | ca. 70 |
| (129) | 1000 | ca. 70 | ca. 70 | ca. 70 | 90-100 | ca. 70 |
| | 300 | ca. 70 | ca. 70 | ca. 70 | 90-100 | ca. 70 |
| (130) | 1000 | ca. 70 | ca. 70 | 90-100 | 90-100 | ca. 70 |
| | 300 | ca. 70 | ca. 70 | ca. 70 | 90-100 | ca. 70 |
| (131) | 1000 | 90-100 | ca. 70 | 90-100 | 90-100 | ca. 70 |
| | 300 | ca. 70 | ca. 70 | 90-100 | 90-100 | ca. 70 |
| (132) | 1000 | ca. 70 | ca. 70 | 90-100 | 90-100 | ca. 70 |
| | 300 | ca. 70 | ca. 70 | 90-100 | 90-100 | ca. 70 |
| (133) | 1000 | 90-100 | 90-100 | 90-100 | 90-100 | 90-100 |
| | 300 | ca. 70 | ca. 70 | 90-100 | 90-100 | 90-100 |
| (136) | 1000 | ca. 70 | ca. 70 | ca. 70 | ca. 70 | 90-100 |
| | 300 | ca. 70 | ca. 70 | ca. 70 | ca. 70 | 90-100 |
| (139) | 1000 | ca. 70 | 90-100 | 90-100 | 90-100 | ca. 70 |
| | 300 | ca. 70 | ca. 70 | ca. 70 | 90-100 | ca. 70 |
| (143) | 1000 | 90-100 | ca. 70 | 90-100 | 90-100 | 90-100 |
| | 300 | ca. 70 | ca. 70 | ca. 70 | 90-100 | ca. 70 |
| (145) | 1000 | ca. 70 | ca. 70 | ca. 70 | 90-100 | ca. 70 |
| | 300 | ca. 70 | ca. 70 | ca. 70 | ca. 70 | ca. 70 |
| (146) | 1000 | 90-100 | 90-100 | ca. 70 | 90-100 | 90-100 |
| | 300 | ca. 70 | ca. 70 | ca. 70 | ca. 70 | ca. 70 |
| (148) | 1000 | ca. 70 | 90-100 | 90-100 | 90-100 | 90-100 |
| | 300 | ca. 70 | 90-100 | ca. 70 | 90-100 | 90-100 |
| (149) | 1000 | ca. 70 | ca. 70 | ca. 70 | 90-100 | 90-100 |
| | 300 | ca. 70 | ca. 70 | ca. 70 | 90-100 | 90-100 |
| (150) | 1000 | ca. 70 | 90-100 | 90-100 | 90-100 | 90-100 |
| | 300 | ca. 70 | 90-100 | ca. 70 | 90-100 | 90-100 |
| (151) | 1000 | ca. 70 | ca. 70 | ca. 70 | ca. 70 | 90-100 |
| | 300 | ca. 70 | ca. 70 | ca. 70 | ca. 70 | 90-100 |
| (152) | 1000 | 90-100 | ca. 70 | ca. 70 | ca. 70 | ca. 70 |
| | 300 | ca. 70 | ca. 70 | ca. 70 | ca. 70 | ca. 70 |
| (153) | 1000 | ca. 70 | ca. 70 | ca. 70 | 90-100 | ca. 70 |
| | 300 | ca. 70 | ca. 70 | ca. 70 | ca. 70 | ca. 70 |
| (154) | 1000 | 90-100 | ca. 70 | ca. 70 | 90-100 | 90-100 |
| | 300 | ca. 70 | ca. 70 | ca. 70 | ca. 70 | 90-100 |
| (155) | 1000 | ca. 70 | 90-100 | ca. 70 | 90-100 | 90-100 |
| | 300 | ca. 70 | ca. 70 | ca. 70 | ca. 70 | 90-100 |
| (156) | 1000 | 90-100 | ca. 70 | ca. 70 | 90-100 | 90-100 |
| | 300 | 90-100 | ca. 70 | ca. 70 | 90-100 | 90-100 |
| (157) | 1000 | 90-100 | ca. 70 | ca. 70 | 90-100 | 90-100 |
| | 300 | ca. 70 | ca. 70 | ca. 70 | ca. 70 | 90-100 |
| (158) | 1000 | ca. 70 | ca. 70 | ca. 70 | ca. 70 | 90-100 |
| | 300 | ca. 70 | ca. 70 | ca. 70 | ca. 70 | 90-100 |

EXAMPLE VII

Control of weeds (post-emergence) in the glasshouse.

Compounds according to the invention are used in various quantities against the same weeds as in example VI. The results are recorded in Table C.

TABLE C

| compound no. | quantity (g/ha) | percentage damage to Ca | Ds | Ga | Gp | Pc |
|---|---|---|---|---|---|---|
| (2) | 300 | 90-100 | ca. 70 | ca. 70 | 90-100 | ca. 70 |
| | 100 | ca. 70 | ca. 70 | ca. 70 | ca. 70 | ca. 70 |
| (7) | 300 | 90-100 | ca. 70 | ca. 70 | ca. 70 | 90-100 |
| | 100 | ca. 70 | ca. 70 | ca. 70 | ca. 70 | 90-100 |
| (8) | 300 | 90-100 | 90-100 | 90-100 | 90-100 | 90-100 |
| | 100 | ca. 70 | 90-100 | ca. 70 | ca. 70 | 90-100 |
| | 30 | ca. 70 | 90-100 | ca. 70 | ca. 70 | 90-100 |
| (23) | 300 | 90-100 | 90-100 | 90-100 | 90-100 | 90-100 |
| | 100 | 90-100 | ca. 70 | 90-100 | 90-100 | 90-100 |
| | 30 | ca. 70 | ca. 70 | ca. 70 | ca. 70 | 90-100 |
| (27) | 300 | ca. 70 | 90-100 | ca. 70 | 90-100 | 90-100 |
| | 100 | ca. 70 | ca. 70 | ca. 70 | ca. 70 | 90-100 |
| | 30 | ca. 70 | ca. 70 | ca. 70 | ca. 70 | 90-100 |
| (31) | 300 | 90-100 | 90-100 | 90-100 | 90-100 | 90-100 |
| | 100 | ca. 70 | 90-100 | ca. 70 | ca. 70 | ca. 70 |
| | 30 | ca. 70 | 90-100 | ca. 70 | ca. 70 | ca. 70 |
| (44) | 300 | 90-100 | ca. 70 | ca. 70 | 90-100 | 90-100 |
| | 100 | 90-100 | ca. 70 | ca. 70 | 90-100 | 90-100 |
| (85) | 300 | 90-100 | 90-100 | ca. 70 | ca. 70 | 90-100 |
| | 100 | 90-100 | 90-100 | ca. 70 | ca. 70 | ca. 70 |
| | 30 | 90-100 | 90-100 | ca. 70 | ca. 70 | ca. 70 |
| (86) | 300 | 90-100 | ca. 70 | ca. 70 | ca. 70 | 90-100 |
| | 100 | ca. 70 | ca. 70 | ca. 70 | ca. 70 | 90-100 |
| | 30 | ca. 70 | ca. 70 | ca. 70 | ca. 70 | ca. 70 |
| (106) | 300 | ca. 70 | ca. 70 | ca. 70 | ca. 70 | 90-100 |
| | 100 | ca. 70 | ca. 70 | ca. 70 | ca. 70 | ca. 70 |
| (125) | 300 | ca. 70 | ca. 70 | ca. 70 | 90-100 | 90-100 |
| | 100 | ca. 70 | ca. 70 | ca. 70 | ca. 70 | ca. 70 |
| (130) | 300 | ca. 70 | ca. 70 | ca. 70 | 90-100 | ca. 70 |
| | 100 | ca. 70 | ca. 70 | ca. 70 | 90-100 | ca. 70 |
| | 30 | ca. 70 | ca. 70 | ca. 70 | 90-100 | ca. 70 |
| (131) | 300 | ca. 70 | ca. 70 | 90-100 | 90-100 | ca. 70 |
| | 100 | ca. 70 | ca. 70 | 90-100 | 90-100 | ca. 70 |
| | 30 | ca. 70 | ca. 70 | ca. 70 | ca. 70 | ca. 70 |
| (132) | 300 | ca. 70 | ca. 70 | 90-100 | 90-100 | ca. 70 |
| | 100 | ca. 70 | ca. 70 | 90-100 | 90-100 | ca. 70 |
| | 30 | ca. 70 | ca. 70 | ca. 70 | 90-100 | ca. 70 |
| (133) | 300 | ca. 70 | ca. 70 | 90-100 | 90-100 | 90-100 |
| | 100 | ca. 70 | ca. 70 | ca. 70 | 90-100 | 90-100 |
| (139) | 300 | ca. 70 | ca. 70 | ca. 70 | 90-100 | ca. 70 |
| | 100 | ca. 70 | ca. 70 | ca. 70 | ca. 70 | ca. 70 |
| | 30 | ca. 70 | ca. 70 | ca. 70 | ca. 70 | ca. 70 |
| (148) | 300 | ca. 70 | 90-100 | ca. 70 | 90-100 | 90-100 |
| | 100 | ca. 70 | ca. 70 | ca. 70 | 90-100 | ca. 70 |
| (150) | 300 | ca. 70 | ca. 70 | ca. 70 | 90-100 | 90-100 |
| | 100 | ca. 70 | ca. 70 | ca. 70 | ca. 70 | ca. 70 |
| | 30 | ca. 70 | ca. 70 | ca. 70 | ca. 70 | ca. 70 |
| (151) | 300 | ca. 70 | ca. 70 | ca. 70 | ca. 70 | 90-100 |
| | 100 | ca. 70 | ca. 70 | ca. 70 | ca. 70 | ca. 70 |

EXAMPLE VIII

Selective control of weeds (post-emergence).

Compounds according to the invention are used in the glasshouse in various quantities against the same weeds as in Example V. Moreover, the same crops are present as in Example V. The following results are obtained: Table D.

TABLE D

| compound no. | quantity (g/ha.) | percentage damage to Ca | Ds | Gp | Pc | Ta | Zm | Gh |
|---|---|---|---|---|---|---|---|---|
| (2) | 300 | 90-100 | ca. 70 | 90-100 | ca. 70 | 0-10 | 0-10 | 0-10 |
| (7) | 300 | 90-100 | ca. 70 | ca. 70 | 90-100 | 0-10 | 0-10 | 0-10 |
| (8) | 100 | ca. 70 | 90-100 | ca. 70 | 90-100 | 0-10 | 0-10 | ca. 30 |
| | 30 | ca. 70 | 90-100 | ca. 70 | 90-100 | 0-10 | 0-10 | ca. 30 |
| (27) | 100 | ca. 70 | ca. 70 | 90-100 | 90-100 | 0-10 | 0.-0 | ca. 30 |
| (31) | 100 | ca. 70 | 90-100 | ca. 70 | ca. 70 | 0-10 | 0-10 | 0-10 |
| (36) | 300 | 90-100 | ca. 70 | 90-100 | 90-100 | 0-10 | 0.-0 | ca. 30 |

TABLE D-continued

| compound no. | quantity (g/ha.) | percentage damage to ||||||| 
| | | Ca | Ds | Gp | Pc | Ta | Zm | Gh |
| --- | --- | --- | --- | --- | --- | --- | --- | --- |
| (41) | 300 | 90–100 | ca. 70 | 90–100 | ca. 70 | 0–10 | 0–10 | 0–10 |
| (42) | 300 | 90–100 | ca. 70 | 90–100 | ca. 70 | 0–10 | 0.–0 | 0–10 |
| (43) | 100 | ca. 70 | ca. 70 | 90–100 | 90–100 | 0–10 | 0–10 | ca. 30 |
| (44) | 300 | 90–100 | ca. 70 | 90–100 | 90–100 | 0–10 | 0–10 | 0–10 |
|  | 100 | 90–100 | ca. 70 | 90–100 | 90–100 | 0–10 | 0–10 | 0–10 |
| (86) | 100 | ca. 70 | ca. 70 | ca. 70 | 90–100 | 0–10 | 0–10 | ca. 30 |
|  | 30 | ca. 70 | ca. 70 | ca. 70 | ca. 70 | 0–10 | 0–10 | ca. 30 |
| (87) | 100 | ca. 70 | ca. 70 | ca. 70 | ca. 70 | 0–10 | 0–10 | ca. 30 |
| (126) | 100 | ca. 70 | ca. 70 | ca. 70 | ca. 70 | 0–10 | 0–10 | ca. 30 |
|  | 30 | ca. 70 | ca. 70 | ca. 70 | ca. 70 | 0–10 | 0–10 | 0–10 |
| (133) | 300 | ca. 70 | ca. 70 | 90–100 | 90–100 | 0–10 | ca. 30 | ca. 30 |
|  | 100 | ca. 70 | ca. 70 | 90–100 | 90–100 | 0–10 | ca. 30 | ca. 30 |
| (143) | 100 | ca. 70 | ca. 70 | ca. 70 | ca. 70 | 0–10 | 0–10 | ca. 30 |
|  | 30 | ca. 70 | ca. 70 | ca. 70 | ca. 70 | 0–10 | 0–10 | ca. 30 |
| (149) | 300 | ca. 70 | ca. 70 | ca. 70 | ca. 70 | 0–10 | ca. 30 | ca. 30 |
|  | 100 | ca. 70 | ca. 70 | ca. 70 | ca. 70 | 0–10 | 0–10 | ca. 30 |
| (151) | 100 | ca. 70 | ca. 70 | ca. 70 | ca. 70 | 0–10 | 0–10 | ca. 30 |

EXAMPLE IX

Control of weeds (pre-emergence) in the glasshouse.

Compounds according to the invention are used in a quantity of 3 kg per hectare against the following weeds: *Galinsoga parviflora* (small-flowered g, Gp), *Galium aparine* (cleavers, Ga), *Chenopodium album* (common lambsquarters, Ca) and *Polygonum convolvulus* (wild buckwheat, Pc). Before emergence of the weeds, the sowed soil is sprayed with a spray liquid obtained according to Example IVb and as described in Example V. The herbicidal activity is determined as described in Example V. The damage to the plants in percentage is recorded in Table E below.

TABLE E

| compound no. | percentage damage to ||||
| | Ca | Ga | Gp | Pc |
| --- | --- | --- | --- | --- |
| (1) | 90–100 | 90–100 | 90–100 | 90–100 |
| (2) | 90–100 | 90–100 | 90–100 | ca. 70 |
| (4) | 90–100 | 90–100 | 90–100 | 90–100 |
| (8) | 90–100 | 90–100 | 90–100 | 90–100 |
| (9) | 90–100 | 90–100 | 90–100 | 90–100 |
| (16) | 90–100 | 90–100 | 90–100 | 90–100 |
| (17) | 90–100 | 90–100 | 90–100 | 90–100 |
| (19) | 90–100 | 90–100 | 90–100 | 90–100 |
| (31) | 90–100 | 90–100 | 90–100 | 90–100 |
| (32) | 90–100 | ca. 70 | 90–100 | ca. 70 |
| (41) | ca. 70 | 90–100 | 90–100 | ca. 70 |
| (42) | 90–100 | 90–100 | 90–100 | ca. 70 |
| (43) | 90–100 | 90–100 | 90–100 | 90–100 |
| (44) | 90–100 | 90–100 | 90–100 | 90–100 |
| (45) | ca. 70 | ca. 70 | 90–100 | 90–100 |
| (74) | ca. 70 | 90–100 | 90–100 | 90–100 |
| (75) | 90–100 | 90–100 | 90–100 | ca. 70 |
| (76) | 90–100 | ca. 70 | ca. 70 | 90–100 |
| (78) | 90–100 | 90–100 | ca. 70 | 90–100 |
| (84) | 90–100 | ca. 70 | ca. 70 | 90–100 |
| (85) | ca. 70 | 90–100 | 90–100 | 90–100 |
| (86) | 90–100 | ca. 70 | 90–100 | 90–100 |
| (87) | 90–100 | 90–100 | 90–100 | 90–100 |
| (88) | 90–100 | ca. 70 | ca. 70 | 90–100 |
| (89) | 90–100 | ca. 70 | ca. 70 | 90–100 |
| (92) | 90–100 | 90–100 | 90–100 | 90–100 |
| (95) | 90–100 | ca. 70 | 90–100 | 90–100 |

I claim:

1. A composition having herbicidal and/or plant growth regulating activity, comprising a herbicidal and/or plant growth regulating amount of an active substance in addition to a solid or liquid inert carrier material, characterized in that the active substance is a compound of the general formula:

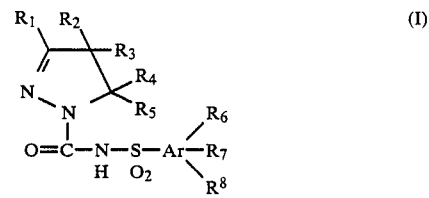

wherein $R_1$, $R_2$, $R_3$ and $R_4$ are equal or different and represent hydrogen atoms, alkyl groups having 1–6 carbon atoms, cycloalkyl groups having 3–6 carbon atoms or alkoxycarbonyl groups having 2–5 atoms;

$R_5$ is a hydrogen atom, an alkyl group or haloalkyl group having 1–8 carbon atoms, an unsubstituted phenyl group or a phenyl group substituted with halogen, nitro, $C_1$–$C_4$ haloalkyl, $C_1$–$C_4$ alkoxy or $C_1$–$C_4$ haloalkoxy, a heterocyclic group selected from the group consisting of furyl and thienyl, which heterocyclic group is unsubstituted or substituted with halogen, nitro, $C_1$–$C_4$ haloalkyl, $C_1$–$C_4$ alkoxy or $C_1$–$C_4$ haloalkoxy, or an alkenyl, alkynyl or alkoxycarbonyl group having 2–5 carbon atoms;

or wherein $R_1$ together with $R_2$ or $R_3$ together with $R_4$ may form a straight or branched alkylene group having 3–5 carbon atoms;

Ar is a phenyl group, a phenyl ($C_1$–$C_4$) alkyl group, a thienyl group or a pyrazolyl group;

$R_6$ is a hydrogen atom or a substituent on Ar, which substituent, in case Ar is a phenyl or phenylalkyl group, is attached to the phenyl group in the ortho position with respect to the sulphonyl or sulphonylalkyl group, and which substituent is selected from the following atoms and groups: a halogen atom; a nitro group; an alkoxycarbonyl group that has 2–8 carbon atoms and is unsubstituted or substituted with one or more hydroxy or $C_1$–$C_4$ alkoxy groups; and an alkyl, hydroxyalkyl, haloalkyl, alkoxy, haloalkoxy, alkylthio, haloalkylthio, alkylsulphonyl and haloalkylsulphonyl group having 1–6 carbon atoms;

$R_7$ is a hydrogen atom, a halogen atom or a $C_1$–$C_4$ alkyl group; and $R_8$ is a hydrogen atom, a halogen atom or a $C_1$–$C_4$ alkyl group; or a salt of this compound with an inorganic o organic base.

2. A composition as claimed in claim 1, wherein the active substance is a compound of the general formula:

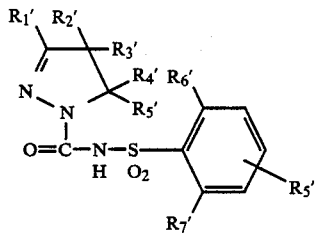
(II)

wherein
$R_1'$, $R_2'$, $R_3'$ and $R_4'$ are equal or different and represent hydrogen atoms or alkyl groups having 1–4 carbon atoms, or wherein $R_1'$ together with $R_2'$, or $R_3'$ together with $R_4'$ form a tetramethylene group, $R_5'$ is a hydrogen atom, a halogenated or non-halogenated alkyl group having 1–8 carbon atoms, a phenyl group, or a phenyl group substituted with halogen, nitro, $C_1$–$C_4$ alkyl or $C_1$–$C_4$ alkoxy, $R_6'$ is a halogen atom, a nitro group, an alkoxycarbonyl group having 2–5 carbon atoms, or a haloalkyl, alkoxy, haloalkoxy, alkylthio, haloalkylthio or alkylsulphonyl group having 1–4 carbon atoms, and $R_7'$ and $R_8'$ are equal or different and represent hydrogen atoms or halogen atoms, or a salt of this compound with an inorganic or organic base.

3. A composition as claimed in claim 1, wherein the active substance is a compound of the general formula:

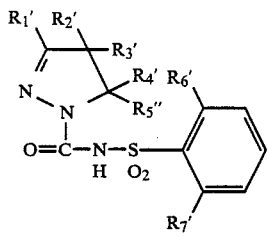
(III)

wherein
$R_1'$, $R_2'$, $R_3'$ and $R_4'$ are equal or different and represent hydrogen atoms or alkyl groups having 1–4 carbon atoms, or wherein $R_1'$ together with $R_2'$, or $R_3'$ together with $R_4'$ form a tetramethylene group, $R_5''$ is an unsubstituted phenyl group or a phenyl group substituted with halogen or nitro, $R_6'$ is a halogen atom, a nitro group, an alkoxycarbonyl group having 2–5 carbon atoms, or a haloalkyl, alkoxy, haloalkoxy, alkylthio, haloalkylthio or alkylsulphonyl group having 1–4 carbon atoms, and $R_7'$ is a hydrogen atom or a halogen atom, or a salt of this compound with an inorganic or organic base.

4. A composition as claimed in claim 1, wherein the active substance is a compound selected from the group consisting of:
1-(2-methoxycarbonylphenylsulphonylcarbamoyl)-3-methyl-2-pyrazoline,
1-(2-methoxycarbonylphenylsulphonylcarbamoyl)-5-ethyl-2-pyrazoline,
1-(2-methoxycarbonylphenylsulphonylcarbamoyl)-5-n-propyl-2-pyrazoline,
1-(2-methoxycarbonylphenylsulphonylcarbamoyl)-4,5-dimethyl-2-pyrazoline,
1-(2-chlorophenylsulphonylcarbamoyl)-5-phenyl-2-pyrazoline,
1-(2-trifluormethylphenylsulphonylcarbamoyl)-5-phenyl-2-pyrazoline,
1-(2,6-difluorophenylsulphonylcarbamoyl)-5-phenyl-2-pyrazoline,
1-(2-methoxycarbonylphenylsulphonylcarbamoyl)-4-ethyl-2-pyrazoline,
1-(2-trifluoromethylphenylsulphonylcarbamoyl)-4-ethyl-2-pyrazoline, 5. A method of controlling and/or preventing undesired plant growth, characterized in that the said plants or their plots are treated with a composition as claimed in any of claims 1–4 in a dose of from 0.01 to 10 kg of active substance per hectare.

6. A method of controlling and/or preventing undesired plant growth, characterized in that the said plants or their plots are treated with a composition as claimed in any of claims 1–4 in a dose of from 0.1 to 3 kg per hectare.

7. An 1-carbamoyl-2-pyrazoline derivative of the general formula I:

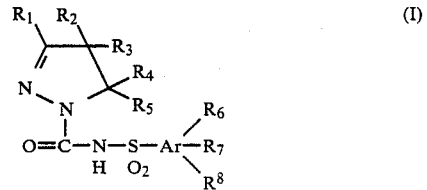
(I)

wherein
$R_1$, $R_2$, $R_3$ and $R_4$ are equal or different and represent hydrogen atoms, alkyl groups having 1–6 carbon atoms, cycloalkyl groups having 3–6 carbon atoms or alkoxycarbonyl groups having 2–5 carbon atoms;

$R_5$ is a hydrogen atom, an alkyl group or haloalkyl group having 1–8 carbon atoms, an unsubstituted phenyl group or a phenyl group substituted with halogen, nitro, $C_1$–$C_4$ haloalkyl, $C_1$–$C_4$ alkoxy, or $C_1$–$C_4$ haloalkoxy, a heterocyclic group selected from the group consisting of furyl and thienyl, which heterocyclic group is unsubstituted or substituted with halogen, nitro, $C_1$–$C_4$ haloalkyl, $C_1$–$C_4$ alkoxy or $C_1$–$C_4$ haloalkoxy, or an alkenyl, alkynyl or alkoxycarbonyl group having 2–5 carbon atoms;

or wherein $R_1$ together with $R_2$ or $R_3$ together with $R_4$ may form a straight or branched alkylene group having 3–5 carbon atoms;

Ar is a phenyl group, a phenyl($C_1$–$C_4$)alkyl group, a thienyl group or a pyrazolyl group;

$R_6$ is a substituent on Ar, which substituent, in case Ar is a phenyl or phenylalkyl group, is attached to the phenyl group in the ortho position with respect to the sulphonyl or sulphonylalkyl group, and which substituent is selected from the following atoms and groups: a halogen atom; a nitro group; an alkoxycarbonyl group that has 2-8 carbon atoms and is unsubstituted or substituted with one or more hydroxy or $C_1$-$C_4$ alkoxy groups; and an alkyl, hydroxyalkyl, haloalkyl, alkoxy, haloalkoxy, alkylthio, haloalkylthio, alkylsulphonyl and haloalkylsulphonyl group having 1-6 carbon atoms;

$R_7$ is a hydrogen atom, a halogen atom or a $C_1$-$C_4$ alkyl group; and $R_8$ is a hydrogen atom, a halogen atom or a $C_1$-$C_4$ alkyl group; or a salt of this compound with an inorganic or organic base.

8. A compound as claimed in claim 7, of the general formula:

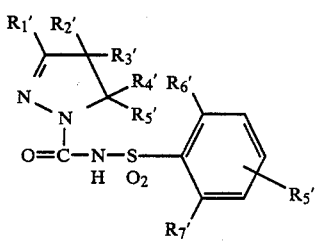

(II)

wherein $R_1'$, $R_2'$, $R_3'$ and $R_4'$ are equal or different and represent hydrogen atoms or alkyl groups having 1-4 carbon atoms, or wherein $R_1'$ together with $R_2'$, or $R_3'$ together with $R_4'$ form a tetramethylene group, $R_5'$ is a hydrogen atom, a halogenated or non-halogenated alkyl group having 1-8 carbon atoms, a phenyl group or a phenyl group substituted with halogen, nitro, $C_1$-$C_4$ alkyl or $C_1$-$C_4$ alkoxy, $R_6'$ is a halogen atom, a nitro group, an alkoxycarbonyl group having 2-5 carbon atoms, or a haloalkyl, alkoxy, haloalkoxy, alkylthio, haloalkylthio or alkylsulphonyl group having 1-4 carbon atoms, and $R_7'$ and $R_8'$ are equal or different and represent hydrogen atoms or halogen atoms, or a salt of this compound with an inorganic or organic base.

9. A compound as claimed in claim 7, of the general formula:

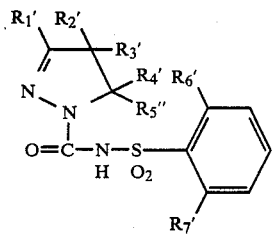

(III)

wherein $R_1'$, $R_2'$, $R_3'$ and $R_4'$ are equal or different and represent hydrogen atoms or alkyl groups having 1-4 carbon atoms, or wherein $R_1'$, together with $R_2'$, or $R_3'$ together with $R_4'$ form a tetramethylene group, $R_5''$ is an unsubstituted phenyl group or a phenyl group substituted with halogen or nitro, $R_6'$ is a halogen atom, a nitro group, an alkoxycarbonyl group having 2-5 carbon atoms, or a haloalkyl, alkoxy, haloalkoxy, alkylthio, haloalkylthio or alkylsulphonyl group having 1-4 carbon atoms, and $R_7'$ is a hydrogen atom or a halogen atom, or a salt of this compound with an inorganic or organic base.

10. A compound selected from the group consisting of:

1-(2-methoxycarbonylphenylsulphonylcarbamoyl)-3-methyl-2-pyrazoline, 1-(2-methoxycarbonylphenylsulphonylcarbamoyl)-5-ethyl-2-pyrazoline, 1-(2-methoxycarbonylphenylsulphonylcarbamoyl)-5-n-propyl-2-pyrazoline, 1-(2-methoxycarbonylphenylsulphonylcarbamoyl)-4,5-dimethyl-2-pyrazoline, 1-(2-chlorophenylsulphonylcarbamoyl)-5-phenyl-2-pyrazoline, 1-(2-trifluoromethylphenylsulphonylcarbamoyl)-5-phenyl-2-pyrazoline, 1-(2,6-difluorophenylsulphonylcarbamoyl)-5-phenyl-2-pyrazoline, 1-(2-methoxycarbonylphenylsulphonylcarbamoyl)-4-ethyl-2-pyrazoline, 1-(2-trifluoromethylphenylsulphonylcarbamoyl)-4-ethyl-2-pyrazoline,

* * * * *